(12) United States Patent
Warner et al.

(10) Patent No.: US 11,769,587 B2
(45) Date of Patent: Sep. 26, 2023

(54) SYSTEMS AND METHODS TO CONFIGURE, PROGRAM, AND PERSONALIZE A MEDICAL DEVICE USING A DIGITAL ASSISTANT

(71) Applicant: GE Precision Healthcare LLC, Wauwatosa, WI (US)

(72) Inventors: Adrian F. Warner, Delafield, WI (US); Dan R. Schneidewend, Menomonee Falls, WI (US); Nicholas P. Nekich, Milwaukee, WI (US); Daniel P. Mabini, Waukesha, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 81 days.

(21) Appl. No.: 16/596,313

(22) Filed: Oct. 8, 2019

(65) Prior Publication Data
US 2021/0104317 A1 Apr. 8, 2021

(51) Int. Cl.
*G16H 40/40* (2018.01)
*G16H 40/63* (2018.01)
*G06F 3/0482* (2013.01)
*G06F 9/445* (2018.01)
*G06F 30/00* (2020.01)

(52) U.S. Cl.
CPC .......... *G16H 40/40* (2018.01); *G06F 3/0482* (2013.01); *G06F 9/44526* (2013.01); *G06F 30/00* (2020.01); *G16H 40/63* (2018.01)

(58) Field of Classification Search
CPC combination set(s) only.
See application file for complete search history.

(56) References Cited

U.S. PATENT DOCUMENTS

| | | |
|---|---|---|
| 6,440,072 B1 | 8/2002 | Schuman et al. |
| 6,475,146 B1 | 11/2002 | Frelburger et al. |
| RE40,116 E | 2/2008 | Engstrom |
| 9,585,562 B2 | 3/2017 | Sobie |
| 2010/0199015 A1 | 8/2010 | Martucci et al. |
| 2016/0333854 A1* | 11/2016 | Lund ...................... F03D 17/00 |
| 2018/0054376 A1* | 2/2018 | Hershey ................ H04L 43/067 |
| 2018/0129959 A1* | 5/2018 | Gustafson .............. G06N 20/00 |
| 2018/0144465 A1 | 5/2018 | Hsieh |
| 2018/0231962 A1* | 8/2018 | Rasheed ............ G05B 23/0283 |
| 2018/0330818 A1 | 11/2018 | Hsieh |
| 2018/0335907 A1* | 11/2018 | Mohan .................... G06F 30/00 |
| 2019/0137982 A1* | 5/2019 | De ................... G05B 19/41885 |
| 2019/0357873 A1* | 11/2019 | Uebler ................... G16H 40/40 |

(Continued)

OTHER PUBLICATIONS

JP application 2020-168969 filed Oct. 6, 2020—Office Action dated Mar. 2, 2022, Machine Translation; 7 pages.

*Primary Examiner* — Hien L Duong

(57) ABSTRACT

Systems, apparatus, instructions, and methods for configuring and controlling medical equipment using a digital assistant are disclosed. An example digital assistant apparatus includes at least one processor to execute the instructions to at least: form a digital model of at least one aspect of a medical equipment; transform the model into a configuration for the medical equipment to perform a task; process input to adjust the configuration; provide the configuration to the medical equipment; monitor execution of the task by the medical equipment; and adjust the configuration of the medical equipment based on the monitored execution.

19 Claims, 18 Drawing Sheets

(56) References Cited

U.S. PATENT DOCUMENTS

| | | | |
|---|---|---|---|
| 2020/0160258 A1* | 5/2020 | Ameri | G06Q 10/10 |
| 2020/0285788 A1* | 9/2020 | Brebner | G06K 9/00979 |
| 2020/0330046 A1* | 10/2020 | Bulut | G16H 50/20 |
| 2020/0342672 A1* | 10/2020 | Schmelig | G06F 3/011 |
| 2020/0358617 A1* | 11/2020 | Baierlein | H04L 63/0807 |
| 2020/0390973 A1* | 12/2020 | Wu | A61M 5/14244 |
| 2020/0401904 A1* | 12/2020 | Voleti | G06N 3/086 |
| 2021/0027136 A1* | 1/2021 | Hwang | G06N 3/082 |
| 2021/0087021 A1* | 3/2021 | Novacek | G05B 19/0428 |
| 2022/0028539 A1* | 1/2022 | von Brasch | H04R 25/558 |

* cited by examiner

SYSTEMS AND METHODS TO CONFIGURE, PROGRAM, AND PERSONALIZE A MEDICAL DEVICE USING A DIGITAL ASSISTANT

FIELD OF THE DISCLOSURE

This disclosure relates generally to configuring medical equipment and, more particularly, to apparatus, systems, and methods to configure, program, and personalize medical equipment using a digital assistant.

BACKGROUND

The statements in this section merely provide background information related to the disclosure and may not constitute prior art.

A clinical or healthcare environment is a crowded, demanding environment that would benefit from organization and improved ease of use of imaging systems, data storage systems, and other equipment used in the healthcare environment. A healthcare environment, such as a hospital or clinic, encompasses a large array of professionals, patients, equipment and computerized information systems. Personnel in a healthcare facility must manage a plurality of patients, systems, and tasks to provide quality service to patients. Healthcare personnel may encounter many difficulties or obstacles in their workflow.

BRIEF DESCRIPTION

Systems, apparatus, instructions, and methods for configuring and controlling medical equipment using a digital assistant are disclosed.

Certain examples provide a digital assistant apparatus including memory including instructions and at least one processor. The example at least one processor is to execute the instructions to at least: form a digital model of at least one aspect of a medical equipment; transform the model into a configuration for the medical equipment to perform a task; process input to adjust the configuration; provide the configuration to the medical equipment; monitor execution of the task by the medical equipment; and adjust the configuration of the medical equipment based on the monitored execution.

Certain examples provide at least one tangible computer-readable storage medium including instructions that, when executed, cause at least one processor to at least: form a digital model of at least one aspect of a medical equipment; transform the model into a configuration for the medical equipment to perform a task; process input to adjust the configuration; provide the configuration to the medical equipment; monitor execution of the task by the medical equipment; and adjust the configuration of the medical equipment based on the monitored execution.

Certain examples provide a computer-implemented method to configure medical equipment using a digital assistant. The example method includes forming a digital model of at least one aspect of a medical equipment. The example method includes transforming the model into a configuration for the medical equipment to perform a task. The example method includes processing input to adjust the configuration. The example method includes providing the configuration to the medical equipment. The example method includes monitoring execution of the task by the medical equipment. The example method includes adjusting the configuration of the medical equipment based on the monitored execution.

DETAILED DESCRIPTION OF CERTAIN EMBODIMENTS

Figure 1:
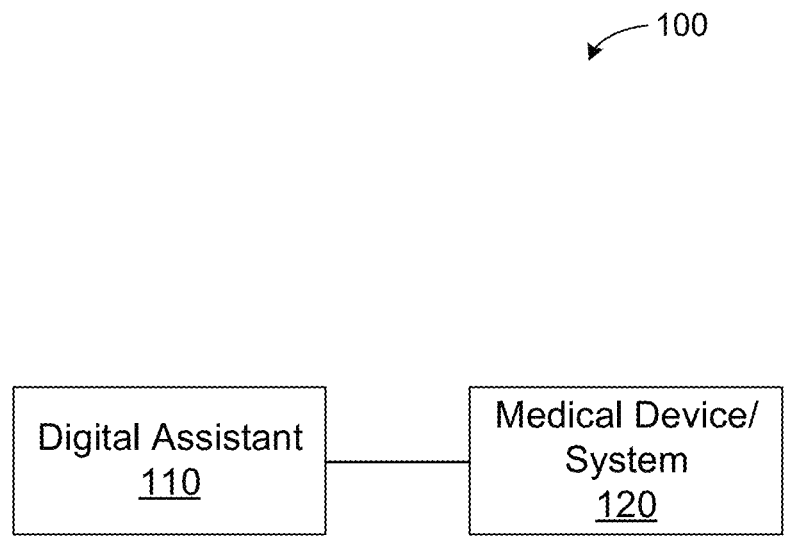
FIG. 1 is a block diagram of an example apparatus including a digital assistant and a medical equipment.

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object.

As used herein, the terms "system," "unit," "module," "engine," etc., may include a hardware and/or software system that operates to perform one or more functions. For example, a module, unit, or system may include a computer processor, controller, and/or other logic-based device that performs operations based on instructions stored on a tangible and non-transitory computer readable storage medium, such as a computer memory. Alternatively, a module, unit, engine, or system may include a hard-wired device that performs operations based on hard-wired logic of the device. Various modules, units, engines, and/or systems shown in the attached figures may represent the hardware that operates based on software or hardwired instructions, the software that directs hardware to perform the operations, or a combination thereof.

As used herein, singular references (e.g., "a", "an", "first", "second", etc.) do not exclude a plurality. The term "a" or "an" entity, as used herein, refers to one or more of that entity. The terms "a" (or "an"), "one or more", and "at least one" can be used interchangeably herein. Furthermore, although individually listed, a plurality of means, elements or method actions may be implemented by, e.g., a single unit or processor. Additionally, although individual features may be included in different examples or claims, these may possibly be combined, and the inclusion in different examples or claims does not imply that a combination of features is not feasible and/or advantageous.

The term "and/or" when used, for example, in a form such as A, B, and/or C refers to any combination or subset of A, B, C such as (1) A alone, (2) B alone, (3) C alone, (4) A with B, (5) A with C, (6) B with C, and (7) A with B and with C. As used herein in the context of describing structures, components, items, objects, and/or things, the phrase "at least one of A and B" is intended to refer to implementations including any of (1) at least one A, (2) at least one B, and (3) at least one A and at least one B. Similarly, as used herein in the context of describing structures, components, items, objects and/or things, the phrase "at least one of A or B" is intended to refer to implementations including any of (1) at least one A, (2) at least one B, and (3) at least one A and at least one B. As used herein in the context of describing the performance or execution of processes, instructions, actions, activities and/or steps, the phrase "at least one of A and B" is intended to refer to implementations including any of (1) at least one A, (2) at least one B, and (3) at least one A and at least one B. Similarly, as used herein in the context of describing the performance or execution of processes, instructions, actions, activities, and/or steps, the phrase "at least one of A or B" is intended to refer to implementations including any of (1) at least one A, (2) at least one B, and (3) at least one A and at least one B.

In addition, it should be understood that references to "one embodiment", "an embodiment", "an example", "one example", "some examples", "certain examples", etc., of the present disclosure are not intended to be interpreted as excluding the existence of additional embodiments/examples that also incorporate the recited features.

Aspects disclosed and described herein provide systems and associated methods to integrate operation and/or structure of a digital assistant with medical equipment such as catheterization lab equipment (e.g., hemodynamic recording instrument, electrophysiology recording instrument, mapping instrument, etc.), imaging device (e.g., x-ray, magnetic resonance (MR), computed tomography (CT), ultrasound, etc.), other medical device, etc. Certain examples facilitate configuration and customization of the medical equipment tailored by a digital assistant based on clinician preference, reason for use, schedule/upcoming appointment, patient, environment, etc. Using the digital assistant, medical equipment can be adapted to fit one or more prescribed and/or environmental/circumstantial limits, and a dialog with a user (e.g., a physician, other healthcare practitioner, etc.) can be facilitated to convey the limitation(s) of the equipment to be used, for example. One or more settings can be adapted across equipment types by the digital assistant such that a medical product can be set to a closest approximation of an equivalent competitive product, for example. Settings can also be proposed by the digital assistant to achieve a better-quality signal recording, image capture, etc., dependent on final acceptance by the user, for example.

As such, certain examples provide a machine learning, deep learning, and/or other artificial intelligence (AI) construct/digital twin to maintain knowledge of machine settings to achieve an objective or function such as capture an image, display a certain type of signal, etc. Certain examples translate a medical device/equipment capability from one vendor configuration to another vendor configuration. Certain examples translate a medical device/equipment capability from one version and/or model to another version and/or model. Certain examples enable and/or transfer expertise on a type of equipment by providing the expertise through the digital assistant capable of verbal query, automated machine identification, etc. Using the digital assistant can reduce a steep learning curve for new or novice users by pooling a body of knowledge from expert users and making this knowledge available on a per machine, such as on a procedure type basis at the direction of a physician, administrator, other user, etc.

Certain examples enable capture of machine settings relative to a user account that has been registered with the digital assistant. Certain examples enable such settings to become part of the user's unique personal profile when used with a piece of equipment under a set of user defined circumstances. Certain examples enable settings held by the digital assistant to be used with similar equipment of differing revision and feature level without user intervention. Certain examples provide feedback to the user regarding features that may be absent or not available with the type, revision, etc., of the equipment in use. Certain examples provide cross-vendor settings such that when a user is operating a different device manufactured by another vendor other than the device/vendor typically used by that user, the digital assistant can propose an alternative set of settings that achieve the same or a close approximation of the same settings on the alternate equipment. Certain examples can establish settings relative to a user-defined procedure and/or can propose settings for user consideration and adoption. Certain examples can hold or store settings and procedure types such that the user can use the setting/procedure type to query the digital assistant to trigger automated installation of the setting/procedure to the device.

In certain examples, the digital assistant serves as a human-machine supplemental interface (e.g., while machine interface(s) remain available for normal key press, macro control type operation, etc., throughout). The digital assistant can be "seeded" with knowledge regarding the equipment by the manufacturer, for example, and initial training can be provided by experts on the equipment, for example. Knowledge of settings and knowledge of applications are used as the basis to form a user experience for applicable medical equipment.

In certain examples, a user profile captures use of medical equipment by a user. The user creates case types and system functions as both static blocks for basic configuration and dynamic interaction sequences where the case types and system functions relate to a healthcare workflow. Storage of these various data types by the digital assistant provides an operational foundation. Additional knowledge sequences around the data types as they relate to various machine model types and software revision levels augment the operational foundation knowledge. Further augmentation can be provided for mapping between competitive equipment types such that the data sets can be used to provide cross-device translation of functionality, for example.

In certain examples, an AI engine used in the digital assistant is then loaded with initial query states for a generic user to initiate a machine learning experience. For example, initial query states can be loaded as trees to form a logical foundation for a user query. Using machine learning algorithms, system usage further trains the digital assistant for knowledge growth in machine setting(s).

In certain examples, the digital assistant receives an instruction from a registered user operating a registered piece of equipment and first records a default status of the equipment when the default status is not already known. A dialog with the user is such that proposed actions are noted and user permission is requested before downloading machine settings into the equipment. The request for permission and acceptance are typical control dialog type actions, for example.

The digital assistant can also be notified by medical equipment of a workflow in progress based on an interpretation of equipment settings, actions, macros, and/or other machine-readable forms of data, for example. The data can be interpreted and used by the digital assistant to propose additional equipment action(s) and/or suggest further configuration(s) that may assist with a task at hand.

Since the digital assistant is physically and computationally independent of the medical equipment, the digital assistant is available to a user almost anywhere where Internet connectivity is available in some form. Thus, knowledge of user preference and user-driven workflow is assimilated by the digital assistant and available to the user at any location, for example.

In certain examples, the digital assistant can serve a plurality of users and equipment. As such, the digital assistant can also correlate functionality across user populations and expert user groups such that the digital assistant can rapidly grow its body of knowledge regarding use of the medical equipment to all users. The digital assistant can also inform when a particular function cannot be performed on certain types of medical equipment. The digital assistant can also ease use learning on equipment by sharing tips and tricks to new users as well as providing a walk-through of product functionality to help a physician and/or other user with routine tasks for the medical equipment, for example.

As such, certain examples simplify equipment operation. Certain examples reduce time to effectiveness on new equipment with expert and novice users. Certain examples configure the digital assistant as a machine learning model/digital twin representing a user, enabling the user to configure machines, teach other users, troubleshoot problems, etc., regardless of location, vendor, version, etc. Translation between equipment types and/or vendor types minimizes or otherwise reduces disruption in cross-vendor applications, for example. Translation between different model and/or software version types helps minimize or otherwise reduce disruption in multi-equipment scenarios such as hospital groups, traveling users, mixed-use scenarios, etc. In certain examples, equipment configuration and use become a knowledge currency that can highlight one device manufacturer relative to another. As such, certain examples model a user-equipment relationship for portable, adaptable, dynamic configuration of medical equipment for a user.

Certain examples provide a sophisticated user experience via a digital assistant based on system configuration, setting, procedural workflow knowledge, etc. In certain examples, the digital assistant model is transparent to machine functionality since the digital assistant can be implemented outside of the equipment itself, which enables a user to use, not use/ignore, and/or modify recommendations, for example. Certain examples augment user documentation through higher-level user interaction knowledge that is hard to document and would otherwise involve significant user training. Certain examples establish improvements in use through user community engagement and best practice sharing without product engineering changes.

FIG. 1 is a block diagram of an example apparatus or system 100 including a digital assistant 110 and a medical equipment 120. The medical equipment 120 can be implemented as an imaging system (e.g., x-ray, MR, CT, ultrasound, positron emission tomography (PET), etc.), a medical device (e.g., an infusion pump, an implant, catheterization equipment, monitor, sensor, etc.), a medical information system (e.g., a picture archiving and communication system (PACS), a radiology information system (RIS), an electronic medical record (EMR) system, a health information system (HIS), a laboratory information system (LIS), a cardiovascular information system (CVIS), etc.), etc. The digital assistant 110 can be implemented as a dedicated hardware device, an application running on a computing device, such as a portable computing device (e.g., a smart phone, a tablet computer, a laptop computer, a smart watch, etc.), a cloud-based system, etc. In certain examples, the digital assistant 110 can be accessible to a user via two or more of these types of devices/systems. For example, the digital assistant 110 can be a cloud-based system accessible to a user via multiple portable computing devices and a dedicated hardware device. In one example, the digital assistant 110 is located in a cloud and can be accessed by a user via his/her phone, via the user's laptop, via the user's tablet, and via a desktop computer in an imaging suite. In another example, the digital assistant 110 is used to customize the user's tablet computer and resides locally on the tablet computer.

The digital assistant 110 is used to access, configure, and facilitate control of the medical equipment 120. The example digital assistant 110 can be used to store and apply one or more configurations for the medical equipment 120, one or more protocols using the medical equipment 120, etc. The example digital assistant 110 can model a protocol, care plan, equipment configuration, equipment type, user preference, etc., and can communicate with the equipment 120 and/or other system to configure, control, and/or execute based on an outcome/output of the model. In certain examples, a user and/or other application, system, device, etc., can approve the modeled output, override the modeled output, adjust the modeled output, etc.

In certain examples, the digital assistant 110 is seeded with certain medical equipment 120. For example, the digital assistant 110 can be seeded with a configuration and/or other settings for a GE CT scanner. The digital assistant 110 can be seeded with other versions of the CT scanner and/or with configuration/setting information for other vendor versions of the CT scanner, for example. In some examples, the digital assistant 110 models the GE CT scanner and then adapts the model when tasked with configuring a different vendor's scanner. For example, the digital assistant 110 can adjust its model of the GE CT scanner v1 to reflect configuration/settings for a GE CT scanner v2. Alternatively or in addition, the digital assistant 110 can adjust its model of the GE CT scanner to reflect configuration/settings for a Philips CT scanner. Thus, the digital assistant 110 can model (e.g., using a digital twin, artificial intelligence model, etc.) the medical equipment 120, identify differences between versions and/or vendors, and translate the model from one version/vendor to another version/vendor based on a protocol, plan, and/or user preference and information regarding equipment configuration, for example.

In certain examples, a digital model or "twin" can be created of a medical equipment to represent and/or be paired with information regarding capabilities, constraints, settings, physics-based models, and/or other configuration information for that piece of medical equipment. For example, a digital representation, digital model, digital "twin", or digital "shadow" is a digital informational construct about a physical system. That is, digital information can be implemented as a "twin" of a physical device/system/person and information associated with and/or embedded within the physical device/system/person. The digital twin is linked with the physical object through the lifecycle of the physical object. In certain examples, the digital twin includes a physical patient in real space, a digital twin of that physical patient that exists in a virtual space, and information linking the physical patient with his/her digital twin. The digital twin exists in a virtual space corresponding to a real space and includes a link for data flow from real space to virtual space as well as a link for information flow from virtual space to real space and virtual sub-spaces.

Machine learning techniques, whether deep learning networks or other experiential/observational learning system, can be used to characterize and otherwise interpret, extrapolate, conclude, and/or complete acquired medical data from a patient, abilities/settings of medical equipment, workflows, environmental constraints, and/or other context, for example. Deep learning is a subset of machine learning that uses a set of algorithms to model high-level abstractions in data using a deep graph with multiple processing layers including linear and non-linear transformations. While many machine learning systems are seeded with initial features and/or network weights to be modified through learning and updating of the machine learning network, a deep learning network trains itself to identify "good" features for analysis. Using a multilayered architecture, machines employing deep learning techniques can process raw data better than machines using conventional machine learning techniques. Examining data for groups of highly correlated values or distinctive themes is facilitated using different layers of evaluation or abstraction.

Deep learning is a class of machine learning techniques employing representation learning methods that allows a machine to be given raw data and determine the representations needed for data classification. Deep learning ascertains structure in data sets using backpropagation algorithms which are used to alter internal parameters (e.g., node weights) of the deep learning machine. Deep learning machines can utilize a variety of multilayer architectures and algorithms. While machine learning, for example, involves an identification of features to be used in training the network, deep learning processes raw data to identify features of interest without the external identification.

Deep learning in a neural network environment includes numerous interconnected nodes referred to as neurons. Input neurons, activated from an outside source, activate other neurons based on connections to those other neurons which are governed by the machine parameters. A neural network behaves in a certain manner based on its own parameters. Learning refines the machine parameters, and, by extension, the connections between neurons in the network, such that the neural network behaves in a desired manner.

A variety of artificial intelligence networks can be deployed to process input data. For example, deep learning that utilizes a convolutional neural network (CNN) segments data using convolutional filters to locate and identify learned, observable features in the data. Each filter or layer of the CNN architecture transforms the input data to increase the selectivity and invariance of the data. This abstraction of the data allows the machine to focus on the features in the data it is attempting to classify and ignore irrelevant background information.

Deep learning operates on the understanding that many datasets include high level features which include low level features. While examining an image, for example, rather than looking for an object, it is more efficient to look for edges which form motifs which form parts, which form the object being sought. These hierarchies of features can be found in many different forms of data such as speech and text, etc.

Learned observable features include objects and quantifiable regularities learned by the machine during supervised learning. A machine provided with a large set of well classified data is better equipped to distinguish and extract the features pertinent to successful classification of new data.

A deep learning machine that utilizes transfer learning may properly connect data features to certain classifications affirmed by a human expert. Conversely, the same machine can, when informed of an incorrect classification by a human expert, update the parameters for classification. Settings and/or other configuration information, for example, can be guided by learned use of settings and/or other configuration information, and, as a system is used more (e.g., repeatedly and/or by multiple users), a number of variations and/or other possibilities for settings and/or other configuration information can be reduced for a given situation.

An example deep learning neural network can be trained on a set of expert classified data, for example. This set of data builds the first parameters for the neural network, and this would be the stage of supervised learning. During the stage of supervised learning, the neural network can be tested whether the desired behavior has been achieved.

Once a desired neural network behavior has been achieved (e.g., a machine has been trained to operate according to a specified threshold, etc.), the machine can be deployed for use (e.g., testing the machine with "real" data, etc.). During operation, neural network classifications can be confirmed or denied (e.g., by an expert user, expert system, reference database, etc.) to continue to improve neural network behavior. The example neural network is then in a state of transfer learning, as parameters for classification that determine neural network behavior are updated based on ongoing interactions. In certain examples, the neural network can provide direct feedback to another process. In certain examples, the neural network outputs data that is buffered (e.g., via the cloud, etc.) and validated before it is provided to another process.

Deep learning machines can utilize transfer learning when interacting with physicians to counteract the small dataset available in the supervised training. These deep learning machines can improve their computer aided diagnosis over time through training and transfer learning. However, a larger dataset results in a more accurate, more robust deployed deep neural network model that can be applied to transform disparate medical data into actionable results (e.g., system configuration/settings, computer-aided diagnosis results, image enhancement, etc.).

Certain examples provide the digital assistant 110 which can leverage one or more deep learning constructs to form one or more digital twins to model the medical equipment 120, model preferences/behavior of a user associated with the digital assistant 110, provide settings/configuration of the medical equipment 120, extrapolate settings/configuration/behavior from one version and/or vendor to another version and/or vendor, etc. As such, the digital assistant 110 can drive medical equipment 120 configuration, use, treatment protocol, care plan, etc., using a digital twin, taken alone and/or in conjunction with one or more deep learning and/or other machine learning models, constructs, devices, etc.

Using the digital assistant 110 and its digital twin and/or other artificial intelligence (AI) model(s), configuration and customization of the medical equipment can be tailored based on clinician preference, reason for use, schedule/upcoming appointment, patient, environment, best practices, other feedback, interpolation, prediction, other modeling, etc. Using the digital assistant 110, medical equipment 120 can be adapted to fit one or more prescribed and/or environmental/circumstantial limits, and a dialog with a user (e.g., a physician, other healthcare practitioner, etc.) can be facilitated to convey the limitation(s) of the equipment to be used, for example. One or more settings can be adapted across equipment types by the digital assistant 110 such that the medical equipment 120 can be set to a closest approximation of an equivalent competitive product, for example. Settings can also be proposed by the digital assistant 110 to achieve a better-quality signal recording, image capture, etc., dependent on final acceptance by the user, for example.

Figure 2:
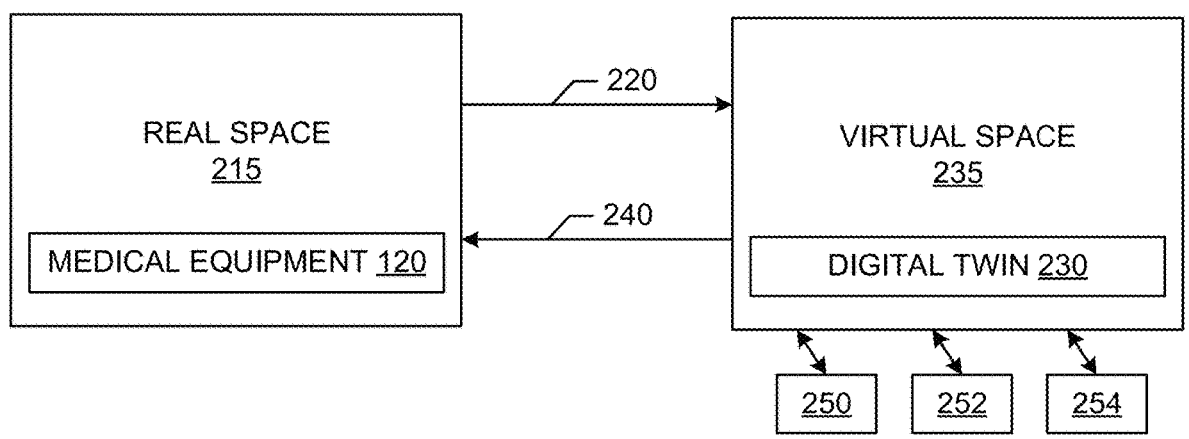
FIG. 2 illustrates an example relationship between the medical equipment and a digital twin of the medical equipment.

FIG. 2 illustrates an example relationship between the medical equipment 120 and a digital twin of the medical equipment. The digital twin can drive configuration, query, operation, integration, etc., of the medical equipment 120, for example. FIG. 2 illustrates the medical equipment 120 in a real space 215 providing data 220 to a digital twin 230 in a virtual space 235. The digital twin 230 and/or its virtual space 235 provide information 240 back to the real space 215. The digital twin 230 and/or virtual space 235 can also provide information to one or more virtual sub-spaces 250, 252, 254. As shown in the example of FIG. 2, the virtual space 235 can include and/or be associated with one or more virtual sub-spaces 250, 252, 254, which can be used to model one or more parts of the digital twin 230 and/or digital "sub-twins" modeling subsystems/subparts of the overall digital twin 230.

In certain examples, one or more health information systems, users, and/or sensors can collect data and relay the collected data 220 to the digital twin 230 (e.g., via self-reporting, using a clinical or other health information system such as a PACS, RIS, EMR, LIS, CVIS, HIS, x-ray imaging system, CT imaging system, MR imaging system, ultrasound imaging system, PET imaging system, and/or combination thereof, etc.). Interaction between the digital twin 230 and the medical equipment 120 can help improve configuration, operation, feedback, etc. An accurate digital description 230 of the medical equipment 120 allows the digital assistant 110 to determine an appropriate configuration and operation for the medical equipment 120 and determine how the equipment 120 fits in a diagnosis and/or treatment protocol, care plan, etc., for a patient, for example.

Figure 3:
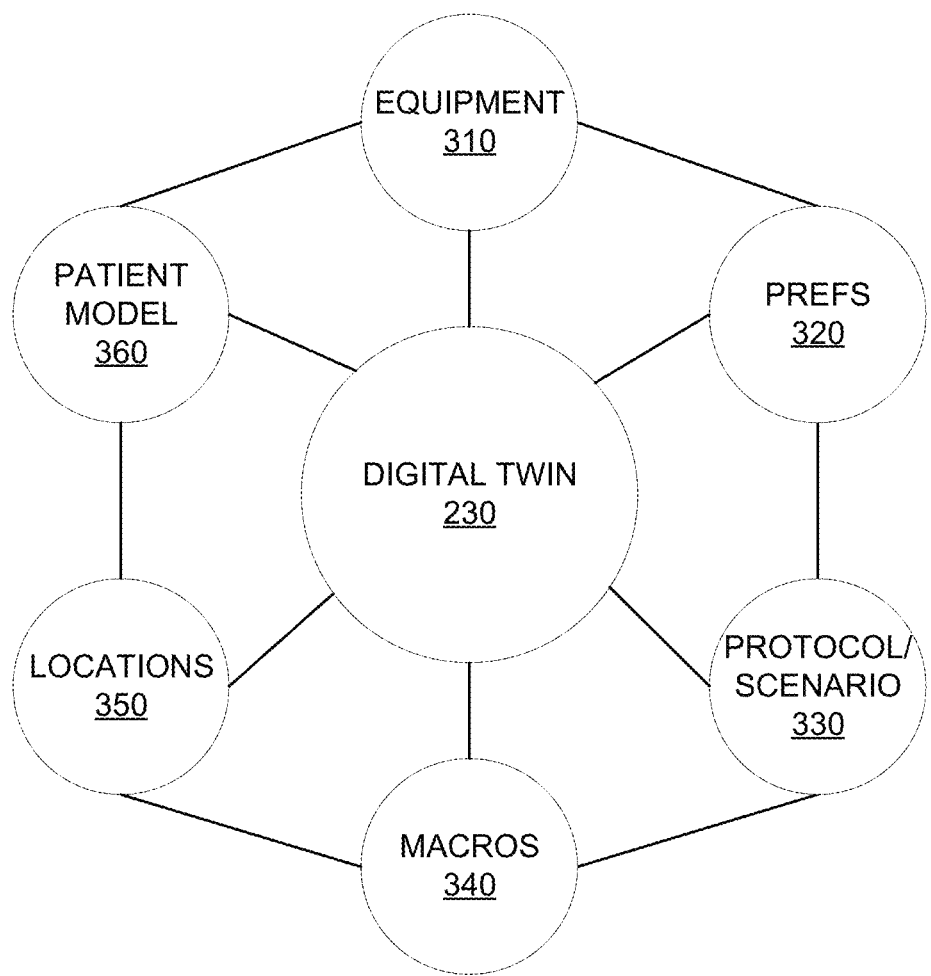
FIG. 3 shows an example digital twin including a plurality of models.

Thus, rather than a generic model, the digital twin 230 is a collection of actual physics-based models reflecting the medical equipment 120 and its associated settings/parameters, operating conditions, use cases, preferred configuration, etc. As shown in the example of FIG. 3, the digital twin 230 can include plurality of models to represent a variety of medical equipment 310, personal preferences 320, protocol/scenario 330, macros and/or routines 340, locations 350, patient model 360, etc. The digital twin 230 can be used to model the medical equipment 120, its configuration and/or use in certain scenarios, translate a configuration from one vendor and/or version to another vendor and/or version, etc., using one or more of the model(s) 310-360. The digital twin 230 can leverage one or more of its models 310-360 to form a configuration for the medical equipment 120 in a scenario/use case to apply an imaging protocol to a patient, for example. In certain examples, the digital twin 230 can be used to model various configurations, scenarios, protocols, etc., to determine a configuration, scenario, protocol, etc., that works best for the equipment 120 and its user and associated patient at a location. While a single digital twin 230 is used in these examples, it is understood that multiple digital twins can be implemented to represent multiple pieces of medical equipment 120, subsystems/subcomponents of medical equipment 120, workflows/protocols, environments/locations, users, patients, etc.

Figure 4:
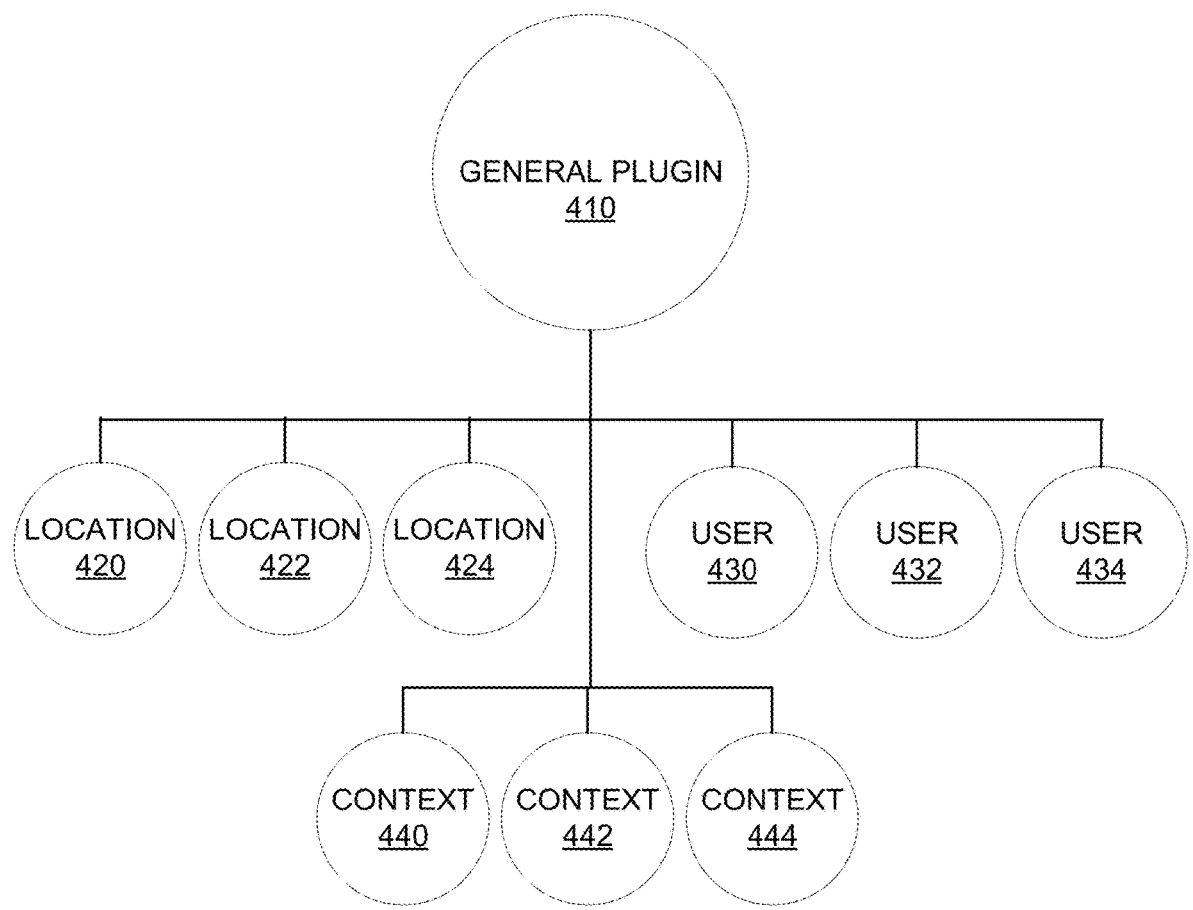
FIG. 4 shows an example plugin hierarchy including a general skill plugin with a plurality of specific plugins.

In certain examples, additional model(s) can be added to the digital twin 230 via plugins and/or other application add-ons to provide new functionality to the digital twin 230 and associated digital assistant 110. The digital twin 230 enables the digital assistant 110 to provide a framework of domain-specific skills to configure and operate the medical equipment 120, for example. The skills can be interactive and flexible to allow the medical equipment 120 to be operated by a variety of users in a variety of situations, for example. As shown in the example of FIG. 4, a general skill plugin 410 can have a plurality of specific plugins 420-444. The plugins 420-428 can be specific to a location 420-424, a user 430-434, a context (e.g., a protocol/scenario) 440-444, etc. As such, a particular plugin 420-444 can be selected from the general skill plugin 410 according to one or more criterion such as location, user, context, etc. The digital assistant 110 can leverage the digital twin 230 to identify and activate the skill plugin 420-444 to configure and operate associated medical equipment 120, for example.

As such, certain examples provide a machine learning, deep learning, and/or other artificial intelligence (AI) digital twin 230 to maintain knowledge of machine settings to achieve an objective or function such as capture an image, display a certain type of signal, etc. Certain examples translate a medical device/equipment capability from one vendor configuration to another vendor configuration. Certain examples translate a medical device/equipment capability from one version and/or model to another version and/or model. Certain examples allow medical equipment 120 and/or an associated user to adapt to capabilities, constraints, etc., of a particular location. Certain examples enable and/or transfer expertise on a type of equipment by providing the expertise through the digital assistant 110 and its digital twin 230 by verbal query, automated machine identification, etc. Using the digital assistant 110 can reduce a steep learning curve for new or novice users by pooling a body of knowledge from expert users in the digital twin 230 and making this knowledge available on an equipment-specific basis, such as based on procedure, protocol, location, type, etc., at the direction of a system, physician, administrator, other user, etc.

Figure 5:
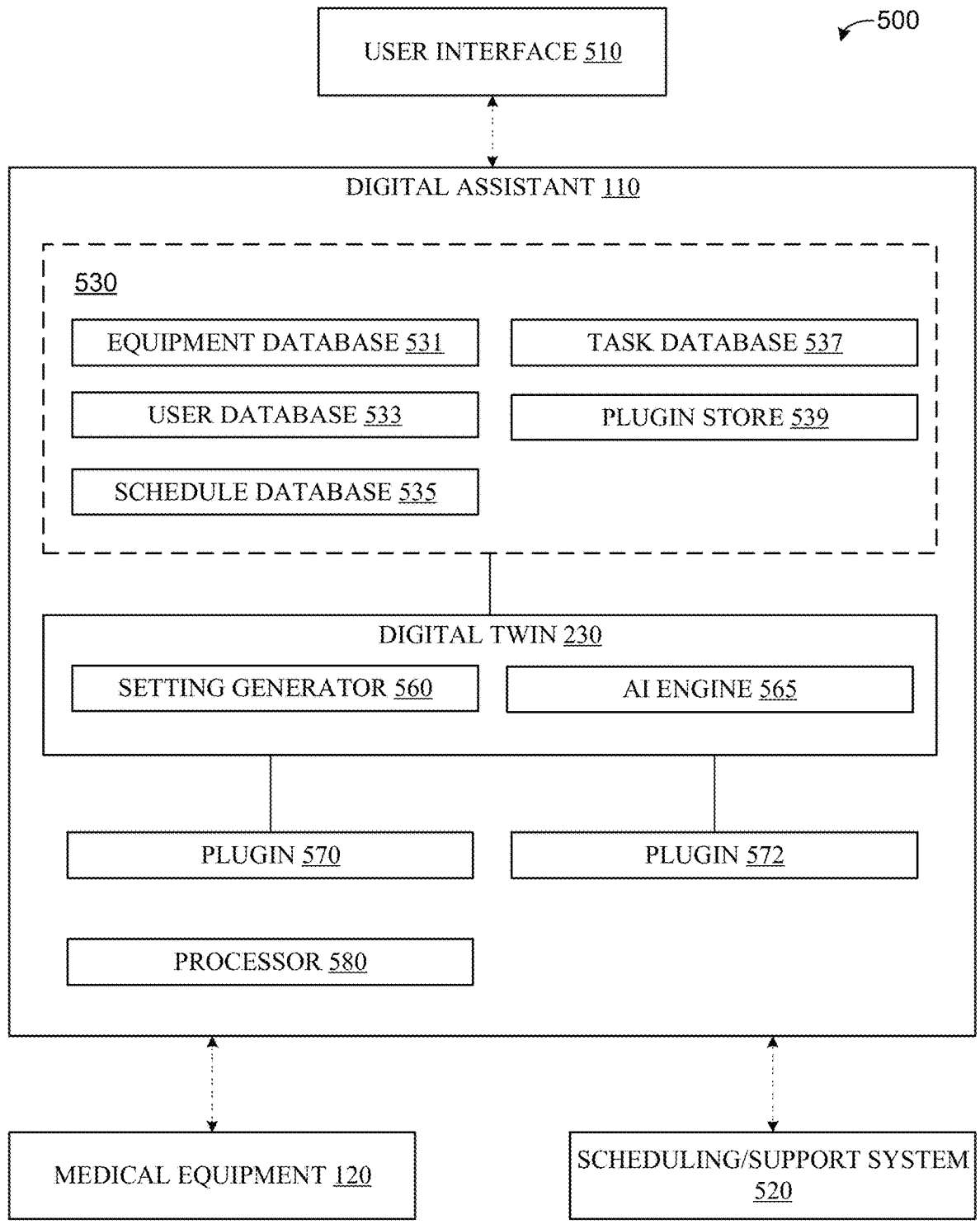
FIG. 5 is an example system including the digital assistant of FIG. 1 in communication with the medical equipment, a user interface, and a scheduling/support system.

FIG. 5 is an example system 500 including the digital assistant 110 in communication with the medical equipment 120, a user interface 510, and a scheduling/support system 520. As shown in the example of FIG. 5, the example digital assistant 110 includes a data store 530 including one or more databases and/or other data stores such as a medical equipment database 531, a user database 533, a schedule database 535, a task database 537, a plugin and/or other add-on data store 539, etc.

The medical equipment database 531 stores information regarding medical equipment 120, such as equipment type, vendor, version, operating manual, commands, settings, other configuration information, etc. The information in the medical equipment database 531 can be leveraged by the digital twin 230 to model and configure the medical equipment 120 for operation, for example. The user database 533 stores information about preferences, profiles, etc., for one or more users associated with the digital assistant 110. The information in the user database 533 can be used by the digital twin 230 to customize the medical equipment 120 for a particular user, for example. The schedule database 535 can be used to store procedure and/or other protocol duration information, calendar information, other scheduling information, etc. The schedule database 535 can be leveraged by the digital twin 230 to schedule a procedure and associated configuration of the medical equipment, for example. The task database 537 can be used to store information regarding tasks to be performed by the medical equipment 120 and/or otherwise included in a protocol, procedure, care plan, etc. The task database 537 can be leveraged by the digital twin 230 to configure the medical equipment 120 and associated protocol, procedure, care plan, etc. The plugin data store 539 can be used to store information about plugins added to the digital assistant 110. For example, a plugin can represent a skill to be added to/learned by the digital twin 230 to be leveraged by the digital assistant 110 to configure the medical equipment 120 and/or other facilitate execution of a healthcare protocol, procedure, care plan, etc.

The digital assistant 110 also includes the digital twin 230, which includes a setting generator 560 to generate settings/configuration for the medical equipment 120 using output from an AI engine 565. The digital twin 230 can interact with one or more plugins and/or other add-ons 570-572 representing added skills, modifications, and/or other model constructs to expand the ability and knowledge of the digital twin 230. For example, one or more skill macros can be learned, added, captured, and/or otherwise provided to the digital twin 230 via the plugins 570-572.

The example digital assistant 110 of FIG. 5 also includes a processor 580 to leverage the digital twin 230, data store 530, etc., to query, configure, control, etc., the medical equipment 120 in response to a trigger, such as user voice command, graphical user interface 510 item selection, application output, other condition, etc. The processor 580 can drive interaction with the medical equipment 120 and the scheduling and/or other support system 520, for example. the processor 580 can receive input from and provide output to the user interface 510, for example. For example, the processor 580 receives an input query or request for medical equipment 120 configuration via the interface 510 and leverages the data store 530 and digital twin 230 to retrieve an appropriate configuration for the medical equipment 120 given an intended patient, intended user, reason for exam and/or associated care plan/protocol, etc.

Figure 6:
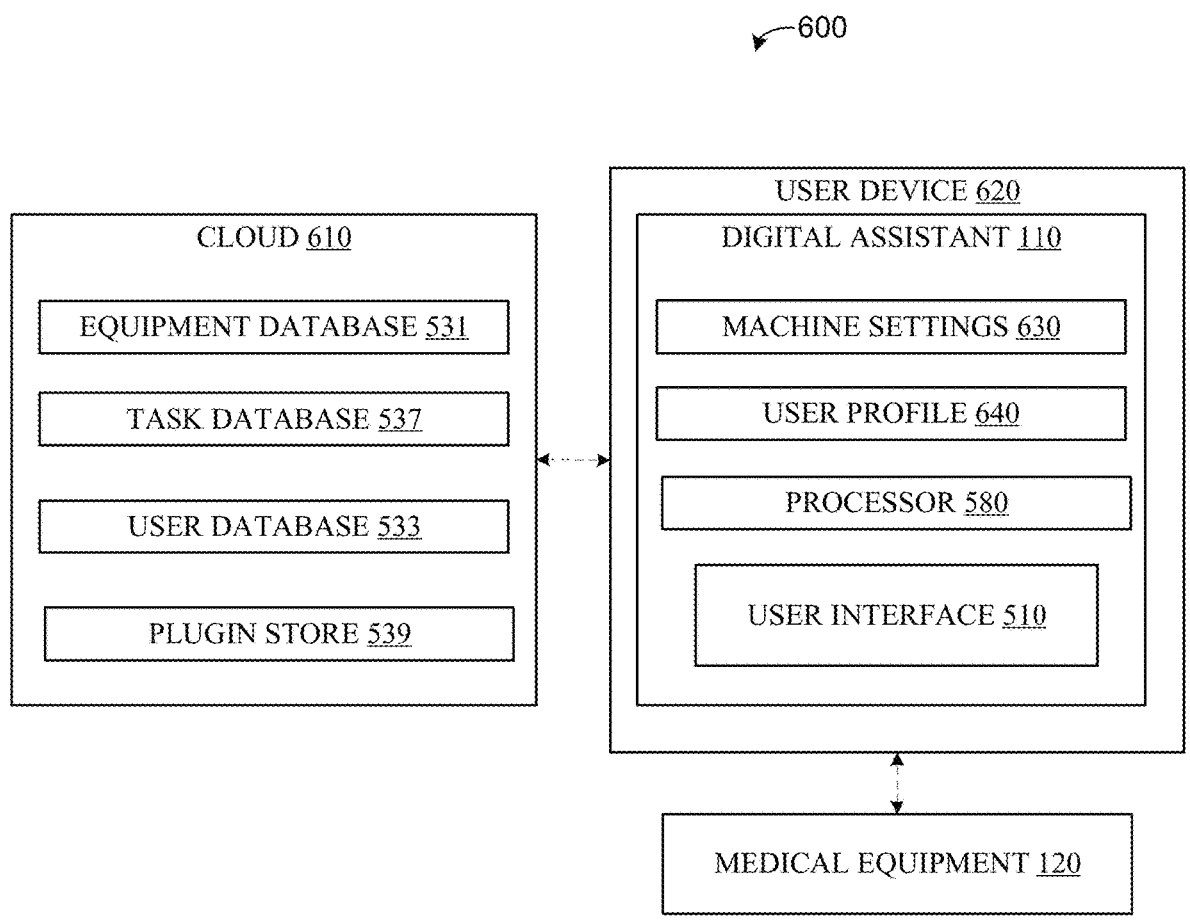
FIG. 6 illustrates an alternative implementation of the apparatus of FIG. 1 in which at least a portion of the digital assistant is located in a cloud sub-system separate from but accessible by the digital assistant.

FIG. 6 illustrates an alternative implementation of the apparatus 600 in which at least a portion of the digital assistant 110 is located in a cloud sub-system 610 separate from but accessible by the digital assistant 110. As shown in the example of FIG. 6, the cloud 610 houses data stores such as the equipment database 531, user database 533, task database 537, plugin data store 539, etc. One or more of the databases 531-539 can be updated by one or more sources in the cloud 610, for example. The example digital assistant 110 of FIG. 6 is instantiated on a user device 620 (e.g., a smartphone, tablet computer, laptop computer, smart watch, etc.) and interacts with the cloud subsystem 610 to generate settings 630 for the medical equipment 120 and maintain a user profile 640 for a user associated with the digital assistant 110, for example. For example, user identification/authentication, role, privileges/authorization, preferences, history, etc., can be maintained as a user profile 640. Data base 531-539 information and user profile 640 preferences can be used by the processor 580 of the digital assistant 110 to drive a configuration for the medical equipment 120, for example. Input to trigger the configuration and provide the configuration to the medical equipment 120 can occur via the user interface 510, for example.

Figure 7:
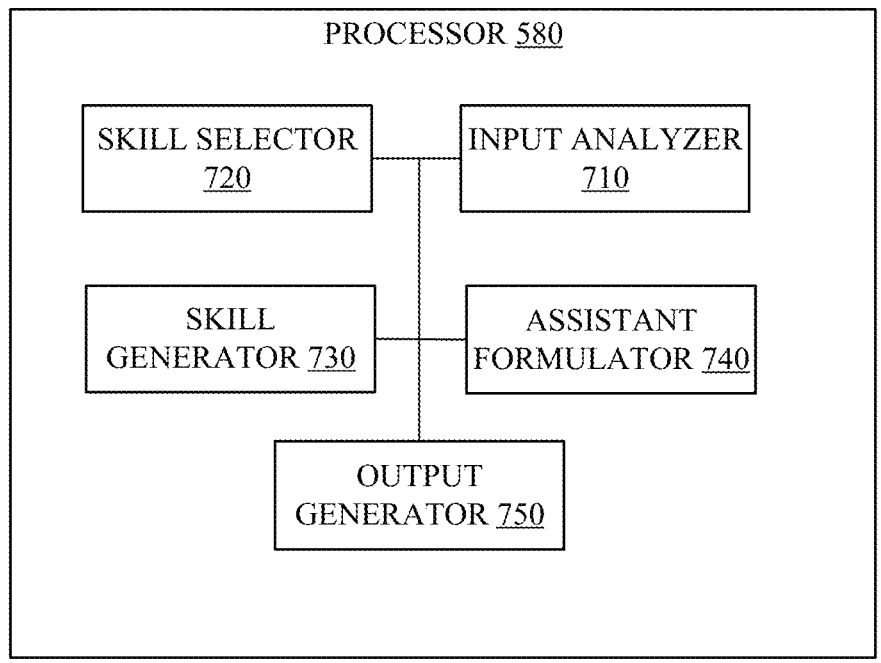
FIG. 7 is a block diagram of an example implementation of the processor of FIG. 5.

FIG. 7 is a block diagram of an example implementation of the processor 580. In the example of FIG. 7, the processor 580 includes an input analyzer 710, a skill selector 720, a skill generator 730, an assistance formulator 740, and an output generator 750. The input analyzer 710 is to process a query, request, trigger, and/or other input received by the digital assistant 110, initiated within the digital assistant 110, etc. The input analyzer 710 transforms an alphanumeric input, key selection, icon selection, gesture input, audio input, application trigger, etc., into actionable command(s) and/or associated query term(s) for execution by the processor 580. For example, a voice command to configure a GE CT scanner can be transformed by the input analyzer 710 into a series of commands and keywords to access a model of the GE CT scanner from the digital twin 230 and/or one or more associated data stores 530 (e.g., the equipment database 531, the user database 533, and the task database 537, etc.) to configure the CT scanner for a particular user, patient, task(s), etc. The input analyzer 710 can also transform input into a new skill to be learned by the processor 580, for example.

The input analyzer 710 triggers the skill selector 720 to select, using the command(s)/keyword(s) generated by the input analyzer 710, one or more skills associated with model(s) of the digital twin 230 and/or one or more plugins 570, 572 of the digital assistant 110. The skill selector 720 can activate, mine, and/or otherwise trigger the digital twin 230 to retrieve skill(s), such as a skill to automate configuration and/or documentation of an interventional catheterization procedure, a skill to automate configuration and/or documentation of a diagnostic catheterization procedure, a skill for pre-case configuration and/or documentation, a skill for post-case configuration and/or documentation, a skill for configuration of an x-ray machine, a skill for configuration of an infusion pump, etc. The skill selector 720 and/or the output generator 750 can configure and/or otherwise customize, further develop, etc., the skill retrieved from the digital twin 230 and/or associated plugin 570, 572 to suit a particular purpose, user, scenario, etc.

The input analyzer 710 can also trigger the skill generator 730 to generate or update a skill to be associated with model(s) of the digital twin 230 and/or one or more plugins 570, 572 of the digital assistant 110, etc. For example, command(s)/keyword(s) captured by the input analyzer 710 can be used to form a new skill learned by the digital twin 230, stored as a plugin 570, 572, etc. In certain examples, user interaction with the medical equipment 120 can be recorded and/or otherwise captured to form a plugin 570, 572 and/or other skill model.

The assistance formulator 740 takes one or more skills selected by the skill selector 720, learned by the skill generator 730, etc., to formulate a configuration for the medical equipment 120 and/or other output (e.g., graphical user interface display, audio output, file transfer to another record system, information system, processing system, etc.). The assistance formulator 740 can formulate assistance by combining skills, customizing skill(s), packaging skill(s) for deployment, etc. The output generator 750 leverages the assistance formed by the assistance formulator 740 to generate an output to the medical equipment 120, to a user, to another system and/or application, etc. For example, the output generator 750 processes assistance formulator 740 output to form setting/parameter value(s), instruction(s)/ command(s), etc., for the medical equipment 120. The output generator 740 provides the output for transmission to the medical equipment 120, for example. As such, the example processor 580 can process input to update skills, leverage skills to generate configuration output, etc.

Figure 8:
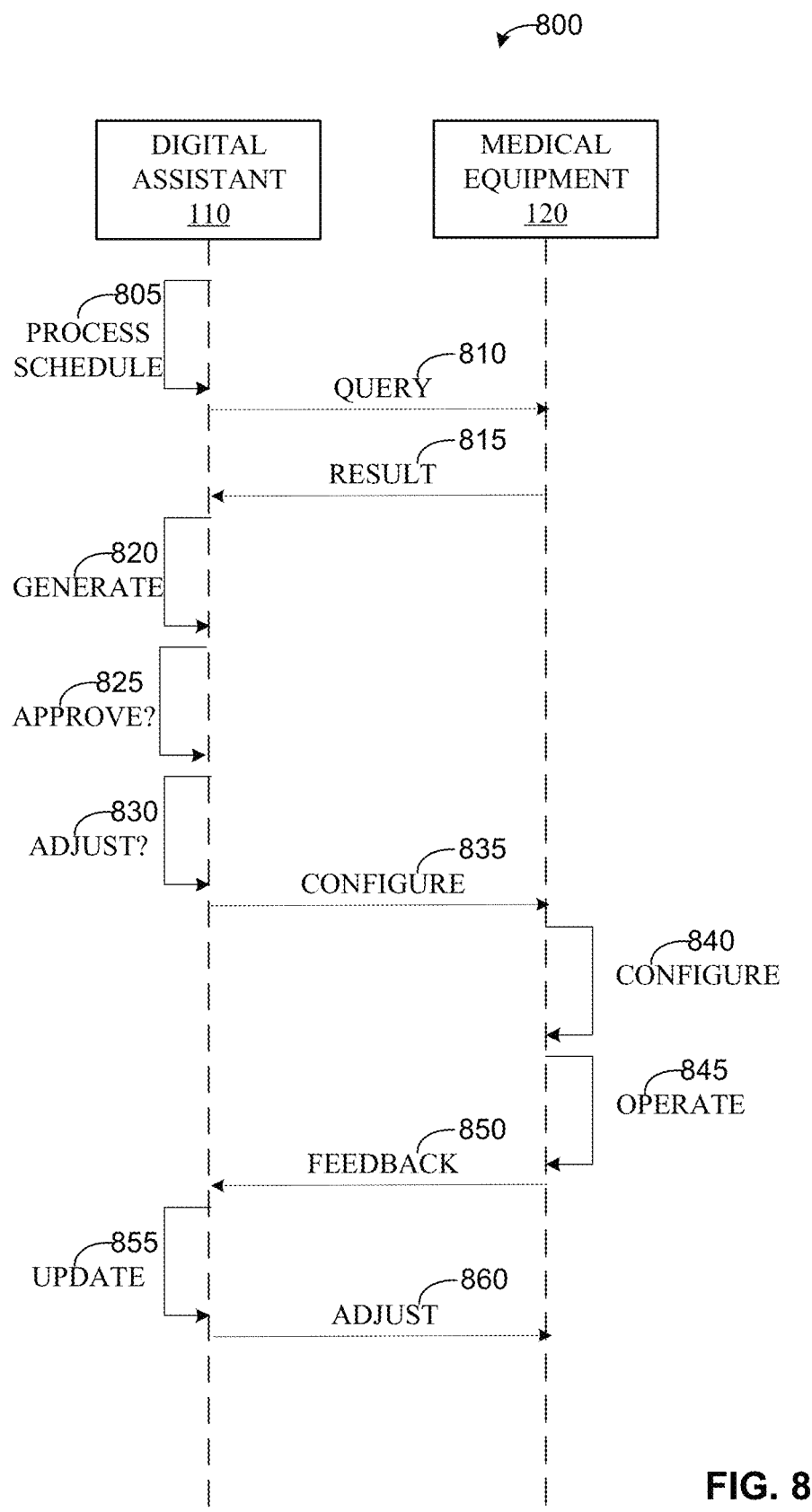
FIGS. 8-10 are data flow diagrams of example data flows between the digital assistant and the medical equipment.

FIG. 8 illustrates a data flow diagram of an example data flow 800 between the digital assistant 110 and the medical equipment 120. At 805, the digital assistant 110 processes a schedule. For example, the digital assistant 110 stores a schedule of upcoming appointments, procedures, other events, etc. For example, the digital assistant 110 stores a schedule indicating an upcoming imaging scan. The imaging scan will use a CT scanner, for example.

At 810, the digital assistant 110 queries the medical equipment 120. For example, the digital assistant 110 queries the medical equipment 120 to determine its type, vendor, version, configurable parameters, etc. At 815, the medical equipment 120 responds to the query/request. For example, the CT scanner provides its type, vendor, version, configurable parameters, etc., to the digital assistant 110.

At 820, the digital assistant 110 generates a skill or configuration based on the information from the medical equipment 120. For example, the digital assistant 110 generates a CT scanner configuration skill based on the information from the CT scanner. The skill saves the equipment type, vendor, version, settings for configurable parameters, etc., in the digital assistant 110, for example. At 825, the digital assistant 110 can provide the skill to a user and/or other system for approval. For example, the configuration of the skill can be displayed via a graphical user interface for user approval, adjustment, deletion, etc. At 830, the skill is approved, deleted, or adjusted based on the input from the user/system. For example, one or more parameters can be adjusted based on user override, input from another application/system, etc. The adjusted configuration can then be saved as a skill with the digital assistant 110 (e.g., as part of the digital twin 230, as a plugin 570, 572, etc.).

At 835, the digital assistant 110 configures the medical equipment 120. For example, based on the schedule, the digital assistant 110 sends a stored configuration (e.g., from the saved skill in the digital twin 230, plugin 570-572, etc.) to the medical equipment 120 to set up the medical equipment 120 for use by a user. For example, the digital assistant 110 can configure the CT scanner for a type of image exam with a particular patient, etc.

At 840, the medical equipment 120 is configured according to the information and/or command from the digital assistant 110. For example, the CT scanner configures itself based on the information/command from the digital assistant such that the CT scanner is ready to obtain images when the patient is positioned with respect to the scanner. At 845, the medical equipment 120 operates according to the configuration. For example, the CT scanner obtains images from a patient as configured by the digital assistant 110.

At 850, the medical equipment 120 provides feedback to the digital assistant 110. For example, radiation exposure information, duration, image quality, etc., can be provided by the CT scanner to the digital assistant 110. At 855, the digital assistant 110 processes the feedback to update a skill, model, and/or configuration information for the medical equipment 120. For example, the digital assistant 110 can update the digital twin 230, plugin 570-572, etc., based on the feedback to reduce/increase exposure time, change dosage, add/remove an image acquisition, adjust setting(s) to improve/reduce image quality, etc. At 860, the digital assistant 110 can provide an adjustment to the medical equipment 120 based on the update. For example, a change in exposure time, dosage, number of acquisitions, other setting, etc., can be provided by the digital assistant 110 to adjust configuration of the medical equipment 120.

The data flow 800 can continue as the digital assistant 110 and medical equipment 120 interact, and the digital assistant 110 can continue to learn from the medical equipment 120 and update models, etc., resulting in a change in configuration in this or a subsequent equipment 120 usage, for example. As such, the example digital assistant 110 can propose a "best" procedure/configuration option to the user based on analysis of the procedure options, current procedure, equipment configuration, etc.

Figure 9:
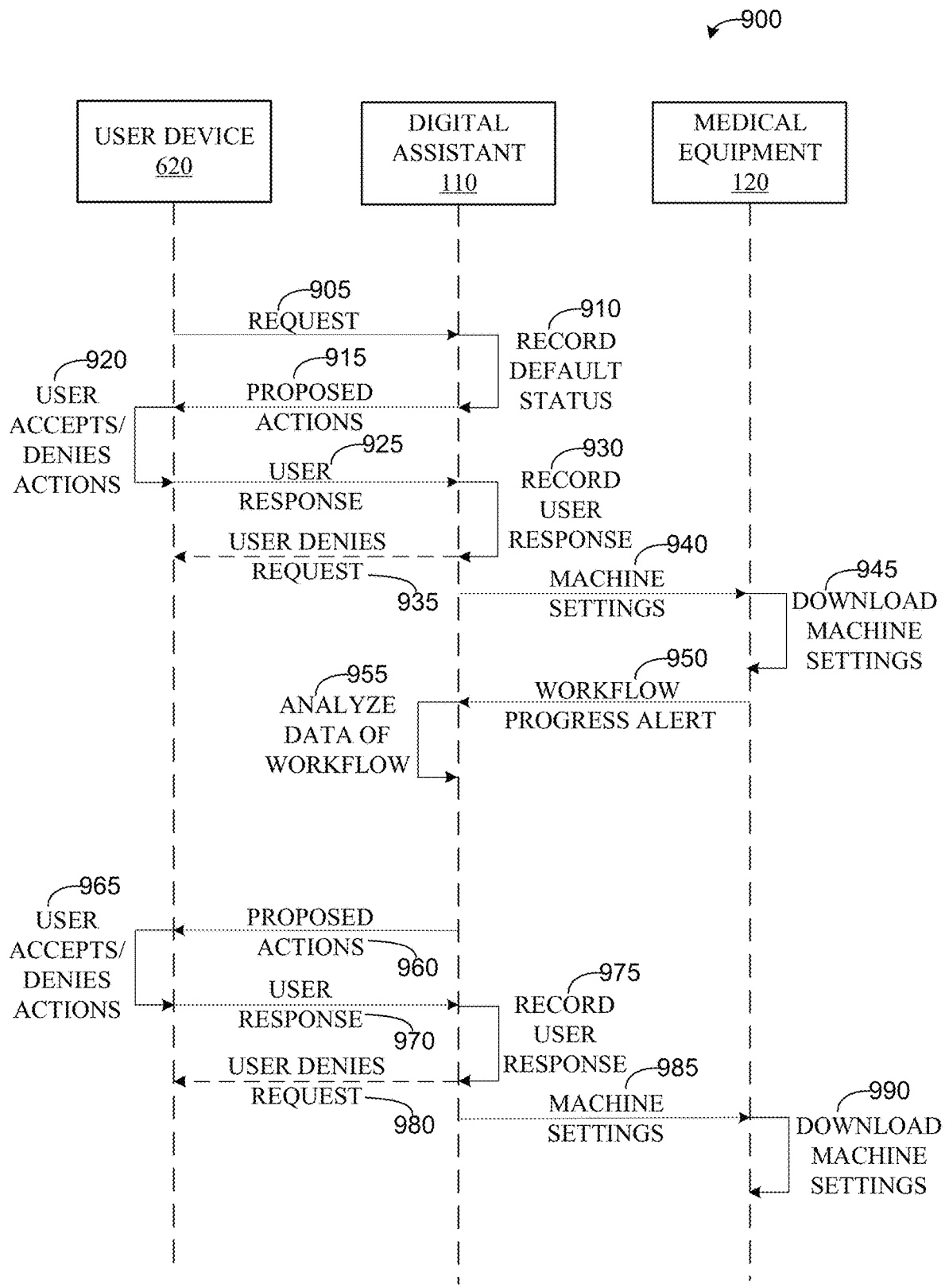

FIG. 9 illustrates a data flow diagram of an example data flow 900 between the user device 620, the digital assistant 110, and the medical equipment 120 to drive medical equipment 120 configuration and operation. At 905, a request is generated from the user device 620 for the digital assistant 110. For example, the user device 620 initiates a connection to the digital assistant 110, a user initiates a request for medical equipment 120 configuration via the user device 620, etc. At 910, the digital assistant 110 records a default status. For example, a default state of the user device 620, the digital assistant 110, an application executing on the user device 620, connected medical equipment 120, scheduled procedure and/or other state of the medical equipment 120, etc., can be recorded as a default status by the digital assistant 110.

At 915, one or more proposed actions are provided by the digital assistant 110 to the user device 620. For example, based on the status, the digital assistant 110 can provide one or more actions such as activate the medical equipment 120, configure the medical equipment 120 for a procedure, etc. At 920, a user accepts, denies, or modifies one or more proposed actions via the user device 620. For example, the user can approve configuration of the medical equipment 120, cancel configuration of the medical equipment 120, adjust one or more settings of the proposed configuration of the medical equipment 120, etc. At 925, the user response is provided from the user device 620 to the digital assistant 110. For example, an audible response from the user, captured by a microphone of the user device 620, can be relayed to the digital assistant 110. A selected and/or typed response of the user can be relayed from the user device 620 to the digital assistant 110, for example.

At 930, the user response is recorded by the digital assistant 110. The digital assistant 110 processes the user response from the user device 620 and saves the response to learn and adjust its status and proposed action for the future.

If the user denied the request, then, at 935, control reverts to the user device 620. If the proposed action was approved (and/or modified but approve), then, at 940, the digital assistant 110 provides corresponding machine settings to the medical equipment 120. For example, the digital assistant 110 provides machine settings to configure the medical equipment 120 for image acquisition of a patient. At 945, the medical equipment downloads the machine settings and configures itself accordingly. The machine settings can trigger/initiate operation of the medical equipment 120 according to the settings, for example. As such, download of settings for image acquisition can initiate image acquisition at the medical equipment 120, for example.

At 950, the medical equipment 120 provides a workflow progress alert 950 to the digital assistant 110. For example, the medical equipment 120 can provide a status, progress report (e.g., imaging progress report, etc.), alert/warning, other feedback, etc., to the digital assistant 110. At 955, the digital assistant 110 analyzes the workflow data provided by the medical equipment 120. For example, the digital assistant 110 evaluates exam progress, timing, dosage, image quality, other feedback in comparison to a protocol, reference value, etc., to evaluate whether or not the workflow is proceeding as expected/planned/suggested/required/etc.

Based on the evaluation of the workflow, at 960, the digital assistant 110 can provide one or more proposed actions to the user device 620. For example, the digital assistant 110 can provide proposed action(s) to adjust configuration/operation of the medical equipment 120, adjust the workflow, switch protocol, etc. At 965, the user can accept, deny, or modify the proposed action(s) via the user device 620. At 970, a user response is provided from the user device 620 to the digital assistant 110. At 975, the user response is recorded and processed. Based on the response, at 980, the request is denied and control reverts to the user device 620 or, at 985, the request is granted and updated machine settings are provided to the medical equipment 120. At 990, the medical equipment 120 downloads the machine settings and updates its configuration/operation/etc., based on the updated machine settings.

Figure 10:
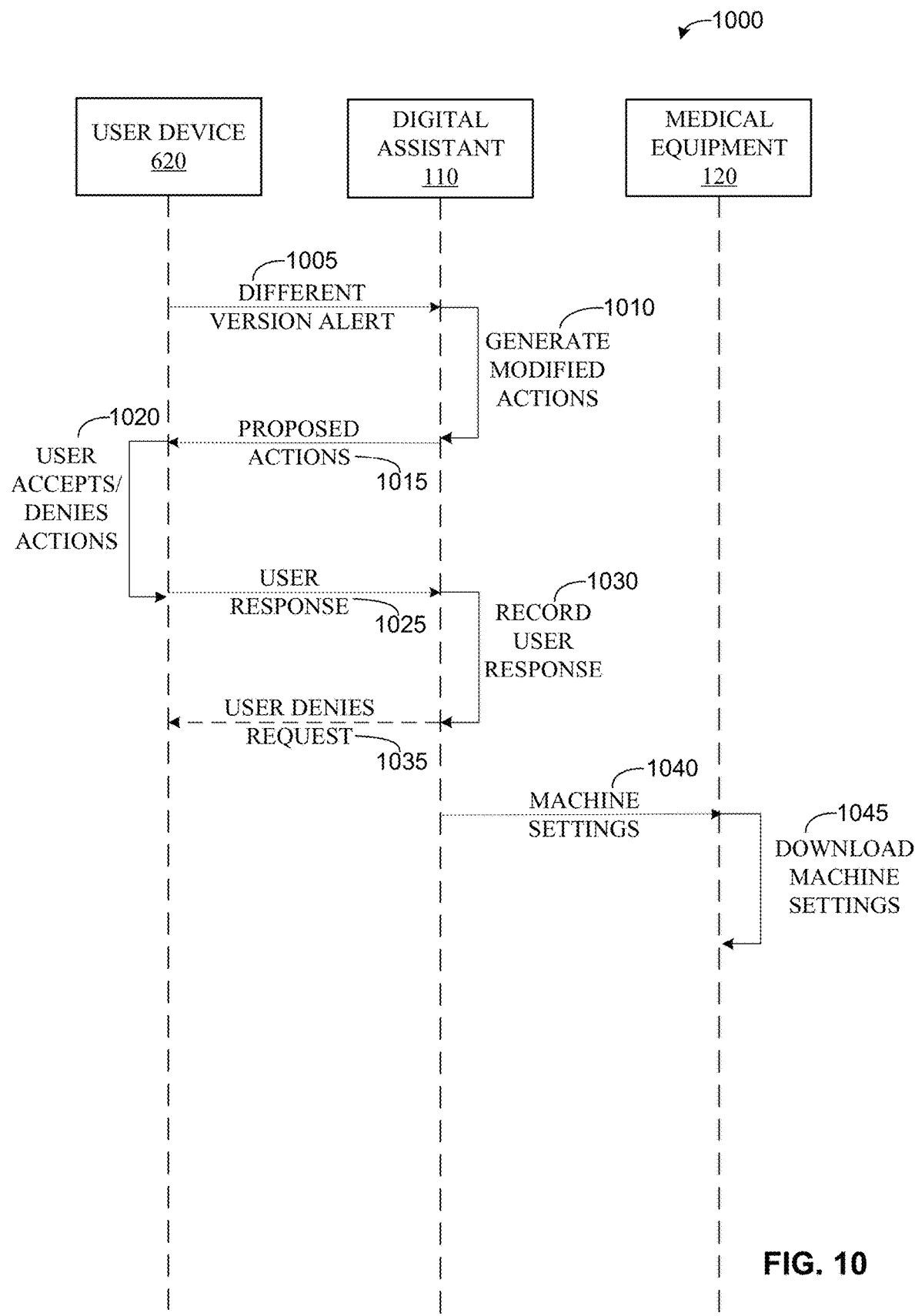

FIG. 10 illustrates a data flow diagram of an example data flow 1000 between the user device 620, the digital assistant 110, and the medical equipment 120 to adjust configuration of the medical equipment 120 based on version, vendor, etc. At 1005, the user device 620 generates a notification to the digital assistant 110 regarding a different version, vendor, etc., of the medical equipment 120. For example, a user familiar with Company A's CT scanner but unfamiliar with Company B's CT scanner is to use Company B's CT scanner. The user accesses the digital assistant 110 from the user device 620 to obtain configuration for Company B's CT scanner. At 1010, the digital assistant 110 generates modified actions based on the request. For example, the digital assistant 110 can look up, translate, and/or otherwise convert configuration information for CT scanner A into configuration information for CT scanner B. As such, the user can be unfamiliar with CT scanner B, and the digital assistant 110 can take the user's preferences, norms, configuration/settings, etc., for CT scanner A and translate/convert them into configuration/settings for CT scanner B using the digital twin 230, plugin 570-572, etc.

At 1015, proposed actions/configuration are conveyed back to the user device 620 by the digital assistant 110 for user confirmation, modification, cancelation, etc. At 1020, the user can accept, deny, modify the proposed actions via the user device 620. For example, the user can override a proposed setting, action, other configuration, etc., accept the suggested configuration, cancel/deny the suggested configuration, etc., for CT scanner B.

At 1025, the user response is transmitted from the user device 620 back to the digital assistant 110. At 1030, the user response is recorded at the digital assistant 110. The response can be used to adjust the digital twin 230, plugin 570-572, other model, etc., for example. The response can be saved for future use in connection with CT scanner B, for example. At 1035, if the user denied the proposed action/configuration, control reverts to the user device 620. At 1040, if the user accepted (and/or modified and accepted) the proposed action/configuration, associated machine settings are provided to the medical equipment 120. At 1045, the medical equipment 120 downloads the settings from the digital assistant 110 to configure the medical equipment 120.

Figure 11:
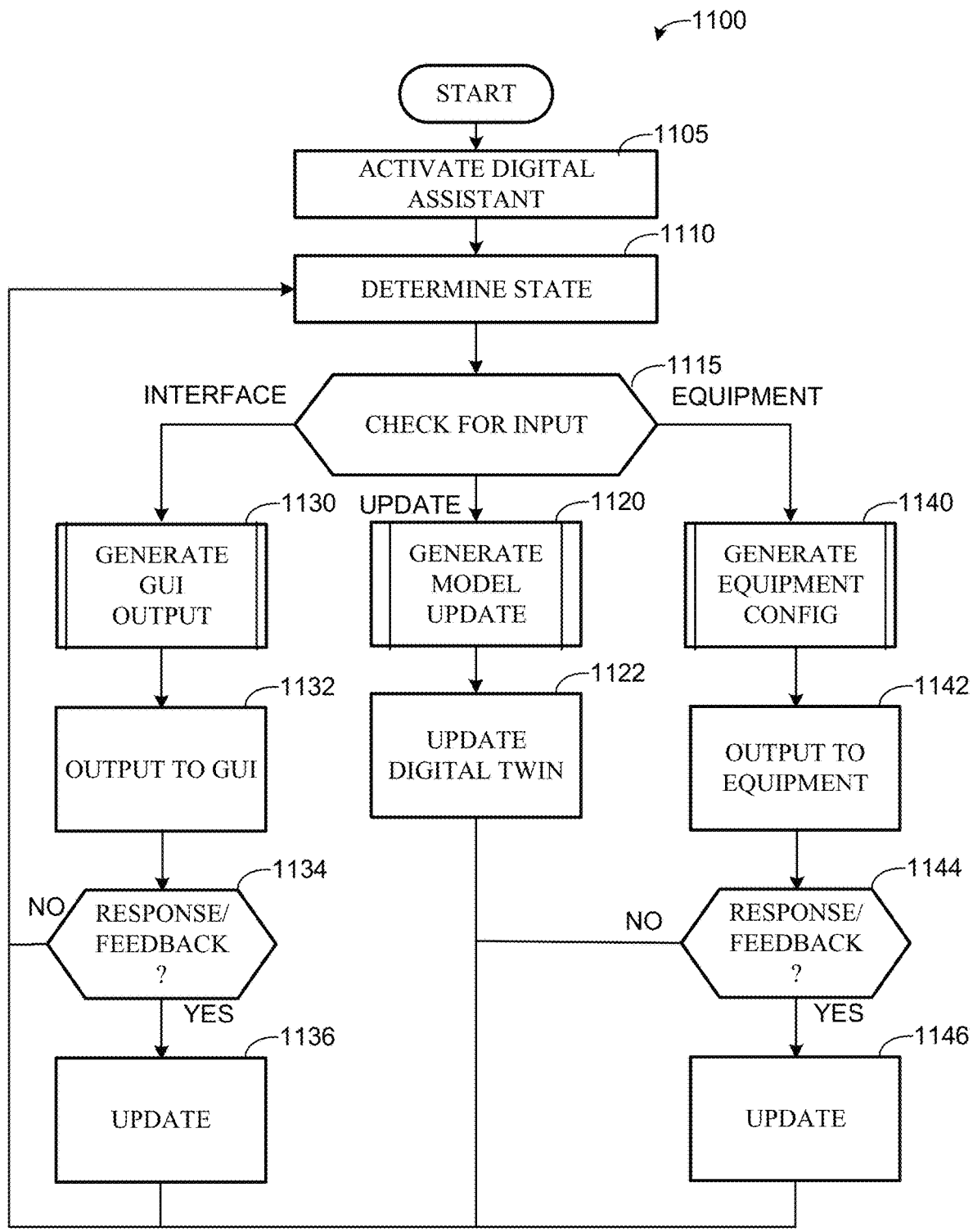
FIGS. 11-15 are flow diagrams of example methods to interact with, learn from, and configure medical equipment, user device, etc., using the example apparatus of FIGS. 1-7.

FIG. 11 is a flow diagram of an example method 1100 to configure and/or control medical equipment 120 using the digital assistant 110. At block 1105, the digital assistant 110 is triggered and/or otherwise activated. For example, the digital assistant 110 can be activated using a wake word, a button press, an option selection, command entry, alert/alarm signal, trigger from the medical equipment 120 and/or other external system/application, etc. At block 1110, the digital assistant 110 determines its state. For example, the digital assistant 110 determines, based on a mode of operation, the digital twin 230, etc., a state of the digital assistant 110 such as in a programming or configuration mode to learn a skill, update a model, etc.; in an operating mode to configure the medical equipment 120, etc.; in an interactive mode to interact with a user, application, and/or other system via the user device 620, etc.; and so on. In certain examples, the digital assistant 110 determines that it is programmed for certain interactions (e.g., providing a schedule to a user, configuring an imaging system, operating an infusion pump, etc.). In certain examples, the digital assistant 110 determines that it needs to model a variation such as in medical equipment 120 type/vendor/version, patient type, procedure update, etc.

At block 1115, the digital assistant 110 awaits and/or checks for input and/or other interaction. For example, if update information is received, then, at block 1120, the digital assistant 110 generates a model update. For example, the digital assistant 110 and its processor 580 can take an input skill plugin 570-572, captured configuration/workflow information, feedback from the medical equipment 120 and/or user device 620, etc., and form an AI model, a training/testing data set, etc., to update the digital twin 230, etc. At block 1122, the digital assistant 110 updates its digital twin 230 using the model update. For example, the digital assistant 110 can add a new skill via a plugin 570-572, update an existing skill by training the digital twin 230 using the AI model, etc. Control then reverts to block 1110 to determine digital assistant 110 state.

If user interface input is received, such as from the user device 620, and/or the mode is to output content to the user device 620, then, at block 1130, a graphical user interface output is generated. For example, a suggested/recommended configuration for the medical equipment 120 can be generated for display and interaction via the graphical user interface 510. At block 1132, the output is provided to an interface, such as the graphical user interface 510 of the user device 620. For example, the generated interface content is provided to the user device 620 to be displayed for interaction via the user interface 510. At block 1134, the user device 620 and/or other user interface is evaluated for a response and/or other feedback generated for the digital assistant 110. If a response and/or other feedback has been provided, then, at block 1136, the feedback and/or other response is provided to the digital assistant 110 to trigger a next action (e.g., a configuration of the medical equipment 120, an adjustment of settings, a cancellation request, etc.), update the digital twin 230 and/or its plugins 570-572, etc. Control then reverts to block 1110 to determine digital assistant 110 state.

If the digital assistant is to configure and/or query the medical equipment 120, then, at block 1140, a configuration for the medical equipment 120 is generated. For example, settings and/or other configuration for the medical equipment 120 can be generated using the digital twin 230 and/or user input. At block 1142, the configuration/setting is output to the medical equipment 120. For example, the generated configuration is provided to the medical equipment 120 to configure the medical equipment 120 for a particular use. Alternatively or in addition, the output can be a query to retrieve settings, configuration, and/or other identifying information from the medical equipment 120 to form and/or update a model of the equipment 120 in the digital twin 230 and/or associated plugin 570-572, for example. At block 1144, the medical equipment 120 is evaluated for a response and/or other feedback generated for the digital assistant 110. If a response and/or other feedback has been provided, then, at block 1146, the feedback and/or other response is provided to the digital assistant 110 to trigger a next action (e.g., a configuration of the medical equipment 120, an adjustment of settings, a cancellation request, etc.), update the digital twin 230 and/or its plugins 570-572, etc. Control then reverts to block 1110 to determine digital assistant 110 state.

Figure 12:
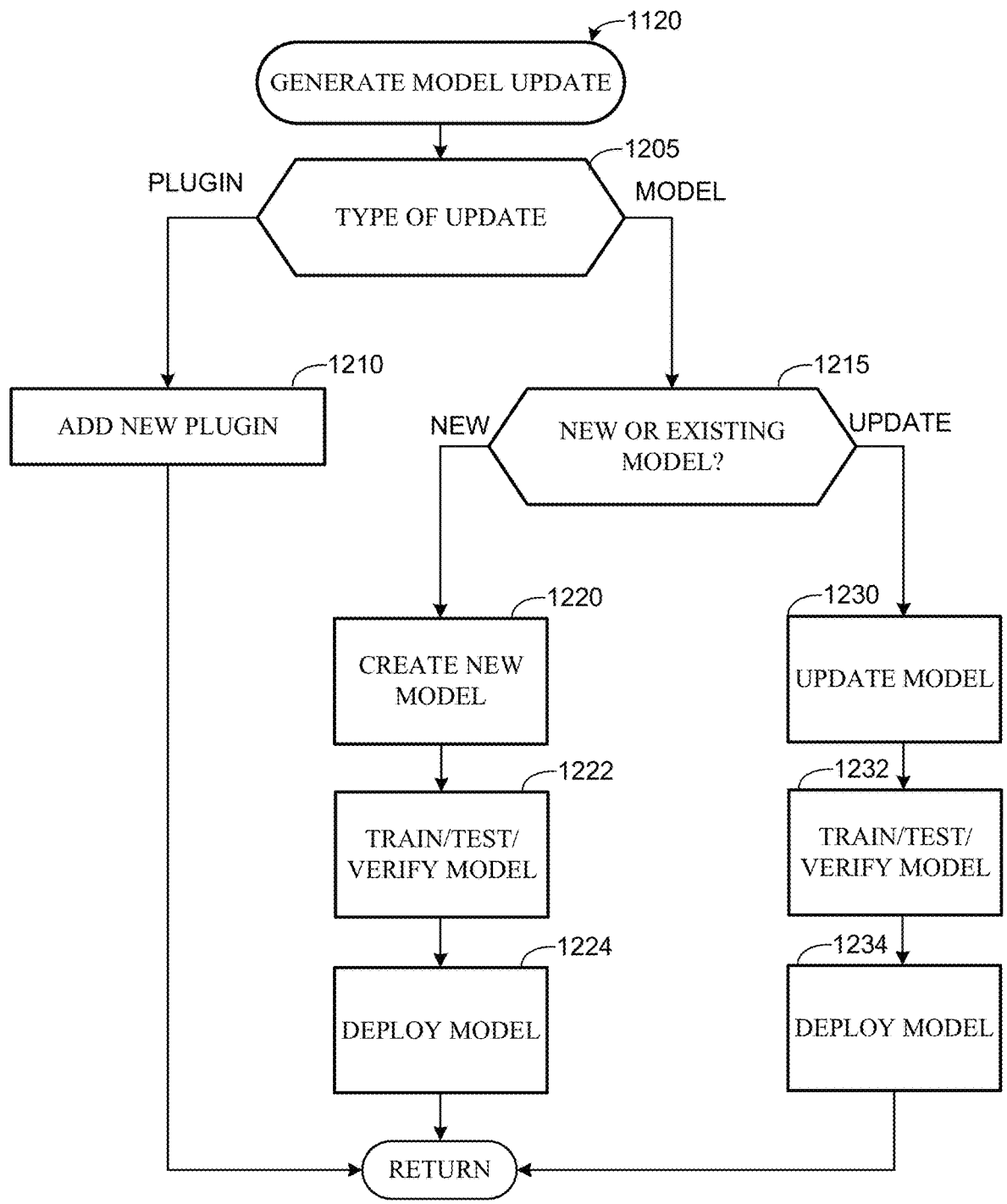

FIG. 12 is a flow diagram of an example method to generate a model update for the digital twin 230 (e.g., block 1120 of the example of FIG. 11). At block 1205, a type of the update is evaluated. If the update is a new plugin, then, at block 1210, the new plugin is added. For example, a macro or skill configured for documentation, hemodynamic and electrophysiology recording, diagnostic catheterization, imaging system configuration, interventional catheterization, infusion pump programming, etc., can be added as a plugin 570-572 to work with the digital twin 230 of the digital assistant 110.

If the update is to a model, then, at block 1215, the update is evaluated to determine whether it is a new model or a change to an existing model. If the update is a new AI model, then, at block 1220, the new model is created. For example, an AI model such as a neural network, random forest, other digital twin, etc., is created according to the rules, parameters, behaviors, boundaries, use case, etc., defined in the update. At block 1222, the new model is trained, tested, and/or verified to help ensure that the model is accurate, robust, repeatable, etc. At block 1224, the new model is deployed for use (e.g., with the digital twin 230, etc.).

If the update is an update to an existing AI model, then, at block 1230, the existing model is updated. For example, an AI model such as a neural network, random forest, other digital twin, etc., can be updated with new parameters/settings, new version, rule(s), use case, etc., as defined in the update. At block 1332, the updated model is trained, tested, and/or verified to help ensure that the model is accurate, robust, repeatable, etc. At block 1234, the updated model is deployed for use (e.g., with the digital twin 230, etc.).

Control then reverts to block 1122 to update the digital twin 230 accordingly with the plugin, model, etc.

Figure 13:
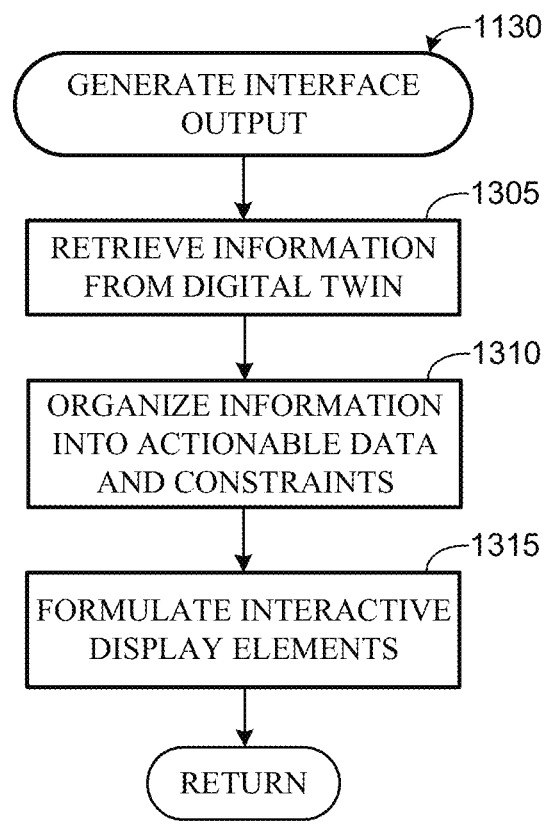

FIG. 13 is a flow diagram of an example method to generate a user interface output using the digital assistant 110 (e.g., block 1130 of the example of FIG. 11). At block 1305, information is retrieved from the digital twin 230, etc., of the digital assistant 110. For example, model(s), data, settings, preferences, and/or other information stored in the digital twin 230, plugin 570-572 and/or data store 530 of the digital assistant 110 is retrieved according to one or more criterion such as a trigger, request, schedule, etc., provided as input at block 1115 of the example of FIG. 11 and/or according to digital assistant 110 state (block 1110 of the example of FIG. 11).

At block 1310, the information is organized into actionable data and/or constraints. For example, a workflow or protocol for catheterization for a patient retrieved from the digital twin 230 is transformed from stored, modeled information into a set of data and associated constraints that are actionable to drive the user interface 510. At block 1315, interactive display elements are formed using the actionable data and constraints. For example, one or more cells, windows, selection boxes, triggers, icons, inputs, graphical representations, etc., are formed to display information and accept feedback/response. The display elements are provided as output to the graphical user interface 510 at block 1132, for example. The display elements can be used to provide a suggested action, request input to select an action, adjust a setting, initiate a query, etc.

Figure 14:
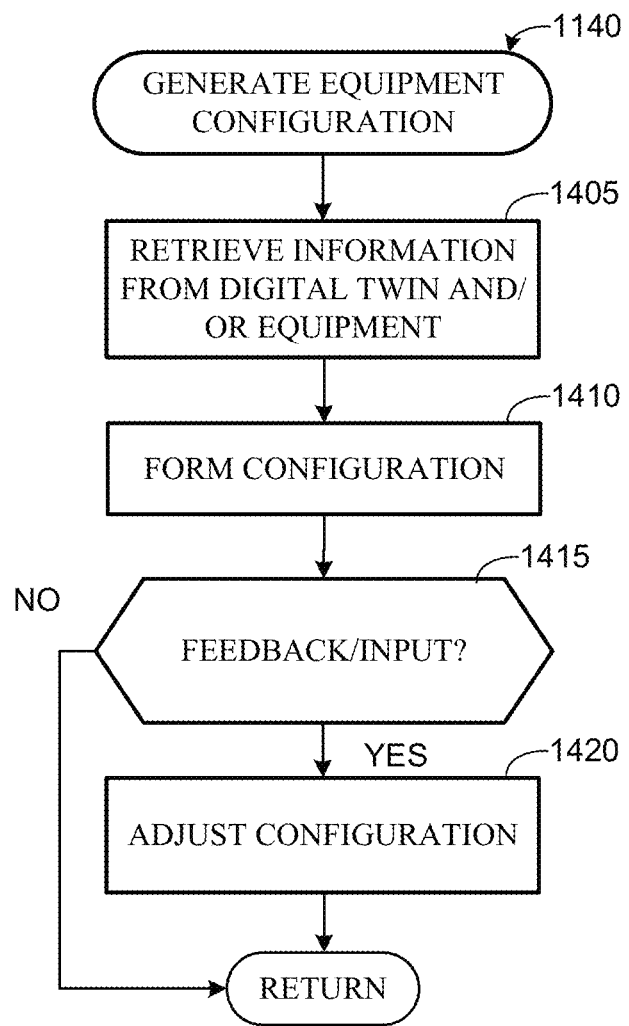

FIG. 14 is a flow diagram of an example method to generate a configuration for the medical equipment 120 using the digital assistant 110 (e.g., block 1140 of the example of FIG. 11). At block 1405, information is retrieved from the digital twin 230, plugin 570-572, data store 530, and/or the medical equipment 120, etc., to form a configuration for the medical equipment 120. For example, information is retrieved from the digital twin 230 regarding configuration of a catheter-based ultrasound system for cardiovascular imaging. A plugin 570-572 can customize the configuration for a particular manufacturer's version of the ultrasound system, for example.

At block 1410, the configuration is formed to configure and/or control the medical equipment. For example, the digital twin 230 model output, plugin 570-572 information, etc., can be combined to generate parameters and/or other settings that can be used to program the medical equipment 120 for operation. For example, configuration settings from the digital twin's model of the catheter-based ultrasound system can be modified by the plugin 570-572 for the particular brand/type of ultrasound system (e.g., a GE catheter-based ultrasound system, etc.) to form a configuration for that particular catheter-based ultrasound system.

At block 1415, feedback and/or other input from the user device 620, medical equipment 120, etc., is verified. For example, the medical equipment 120 can have a status update (e.g., regarding available resources, timing, intensity, quality, etc.) that can be used to adjust equipment 120 settings. Alternatively or in addition, a user preference can supersede a default configuration, for example. If feedback and/or other input exists, then, at block 1420, the configuration is adjusted based on the feedback/input. For example, configuration setting(s) are adjusted based on an update/status/other feedback from the medical equipment 120, user preference/override, etc. The adjusted/updated configuration can then be provided to the medical equipment 120 at block 1142.

As such, one or more models, data constructs, etc., can be combined to generate a configuration for the medical equipment 120, and that configured can be adjusted based on one or more additional factors such as user input, equipment status, other feedback from an application, system, etc., before transmitting the configuration to set up and operate the medical equipment, for example.

Figure 15:
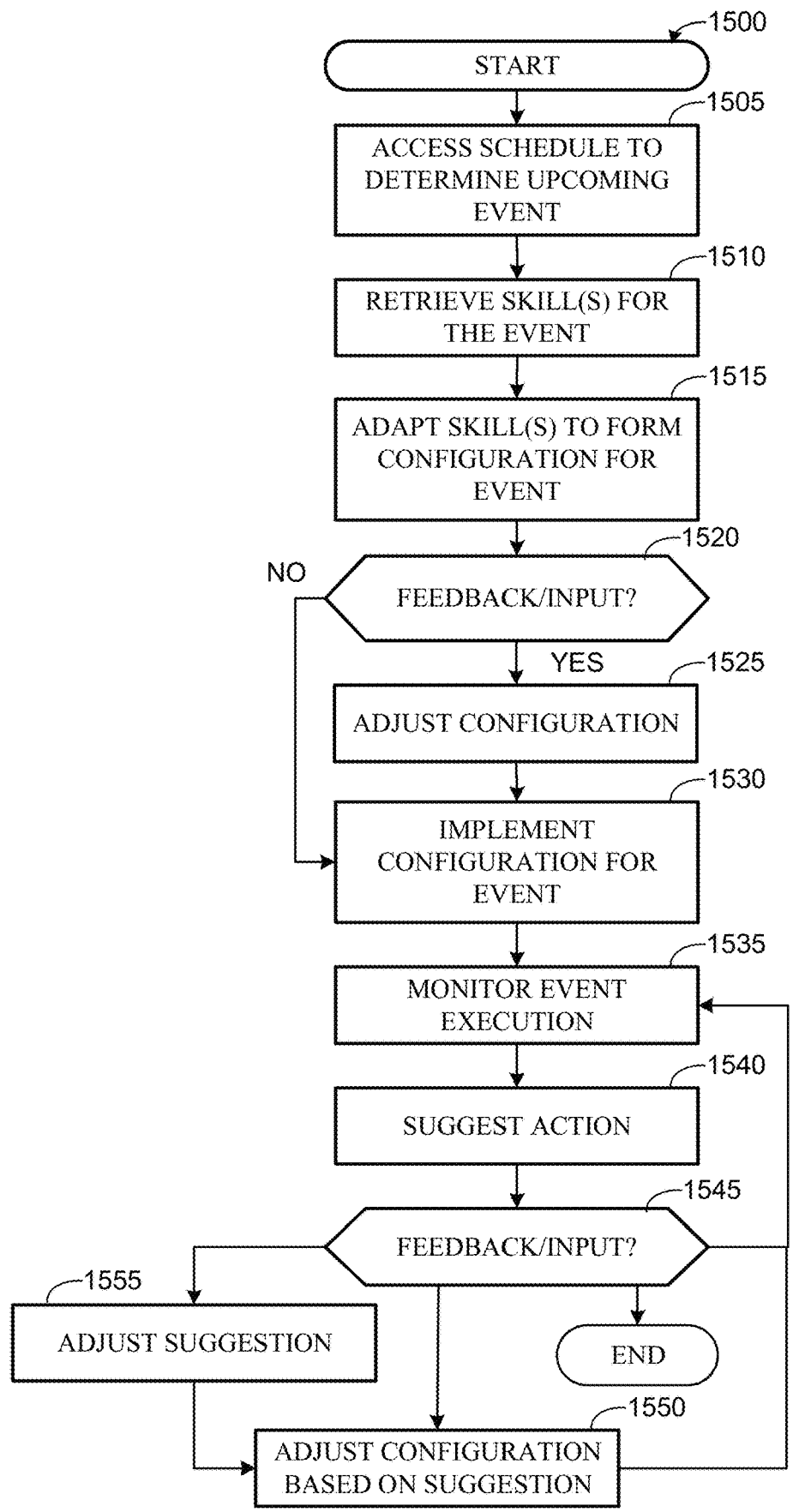

FIG. 15 is a flow diagram of an example process 1500 to drive an assistance framework to dynamically conduct a healthcare workflow using a digital assistant 110. At block 1505, the digital assistant 110 accesses a schedule to determine an upcoming event on the schedule. The schedule can be associated with a user, a location, the medical equipment 120, etc. For example, the schedule may indicate that an ablation procedure is scheduled for the user.

At block 1510, skill(s) and/or other model(s) associated with the event are retrieved. For example, the event can be associated with the medical equipment 120, user device 620, other system, etc., and each device/system can have an associated skill to drive it. For example, the ablation procedure involves a protocol, which can be associated with a skill, and an ablation device, for which a manufacture can have a skill plugin 570-572 to configure the ablation device. The particular location of the procedure can have an additional model of the digital twin 230 associated with the location (e.g., hospital, ward/department, state, country, etc.), for example.

At block 1515, the retrieved skill(s) and/or model(s) are adapted based on the combination of skill(s) and/or model(s) along with user preferences, other constraints (e.g., regulatory, usage-based, location-based, etc.), etc., to form a configuration for the event. For example, the ablation protocol skill, ablation device skill, and location model are adapted in combination to form a configuration for the event. As such, the ablation device can be configured according to its plugin 570-572 as adjusted for the particular protocol, location constraint, user preference, etc.

At block 1520, the configuration is displayed for interaction and feedback. For example, the configuration is provided to the user interface 510, and the user can accept, cancel, edit, etc. If edit/adjustment feedback is provided, then, at block 1525, the configuration is adjusted based on the feedback. For example, the user adjusts a temperature or intensity setting for the ablation device, and the ablation device configuration is updated accordingly.

At block 1530, the configuration is implemented for the event. For example, the ablation device can be set up according to the configuration, and the user can be guided through the ablation procedure via the user interface 510 according to the configuration. At block 1535, execution of the event is monitored. For example, the digital assistant 110 monitors progress of the ablation procedure and reacts to the procedure to suggest a next action, adjust a next action, adjust the configuration, etc. As such, at block 1540, the digital assistant 110 can suggest a correction, adjustment, next action, etc. For example, the digital assistant 110 can suggest and/or otherwise prompt the user to change a setting of the ablation device based on feedback gathered from the use of the ablation device in the procedure, etc.

At block 1545, the digital assistant 110 adjusts operation based on feedback to the suggestion. For example, if the suggestion is accepted, then, at block 1550, the suggestion is implemented to adjust the configuration. If there are edits to the suggestion, then, at block 1555, the suggestion is edited before being applied to the event configuration at block 1550. If the suggestion is denied, then the event configuration continues. If the event is complete, then the process ends.

As such, certain examples enable creation of skills, models, plugins, etc., to drive configuration and operation of medical equipment 120 and associated workflows using the digital assistant 110. Certain examples provide a framework for dynamic configuration of a variety of medical equipment 120 tailored to a variety of workflows, users, locations, patients, regulatory environments, etc. The digital assistant 110 and its digital twin 230 provide a digital intelligence to learn about a location/environment, a user, leverage best practices, etc. Based on location, for example, the digital assistant 110 can provide a different answer to the same question. For example, weather, available equipment, distance, etc., can vary by location, while a schedule for a protocol/procedure remains the same. The similarities and differences can drive a customized configuration and guidance for a particular event/use case. An interactive workflow experience can be tailored by the digital assistant 110 to personalize equipment 120 and tasks for the user.

Figure 16:
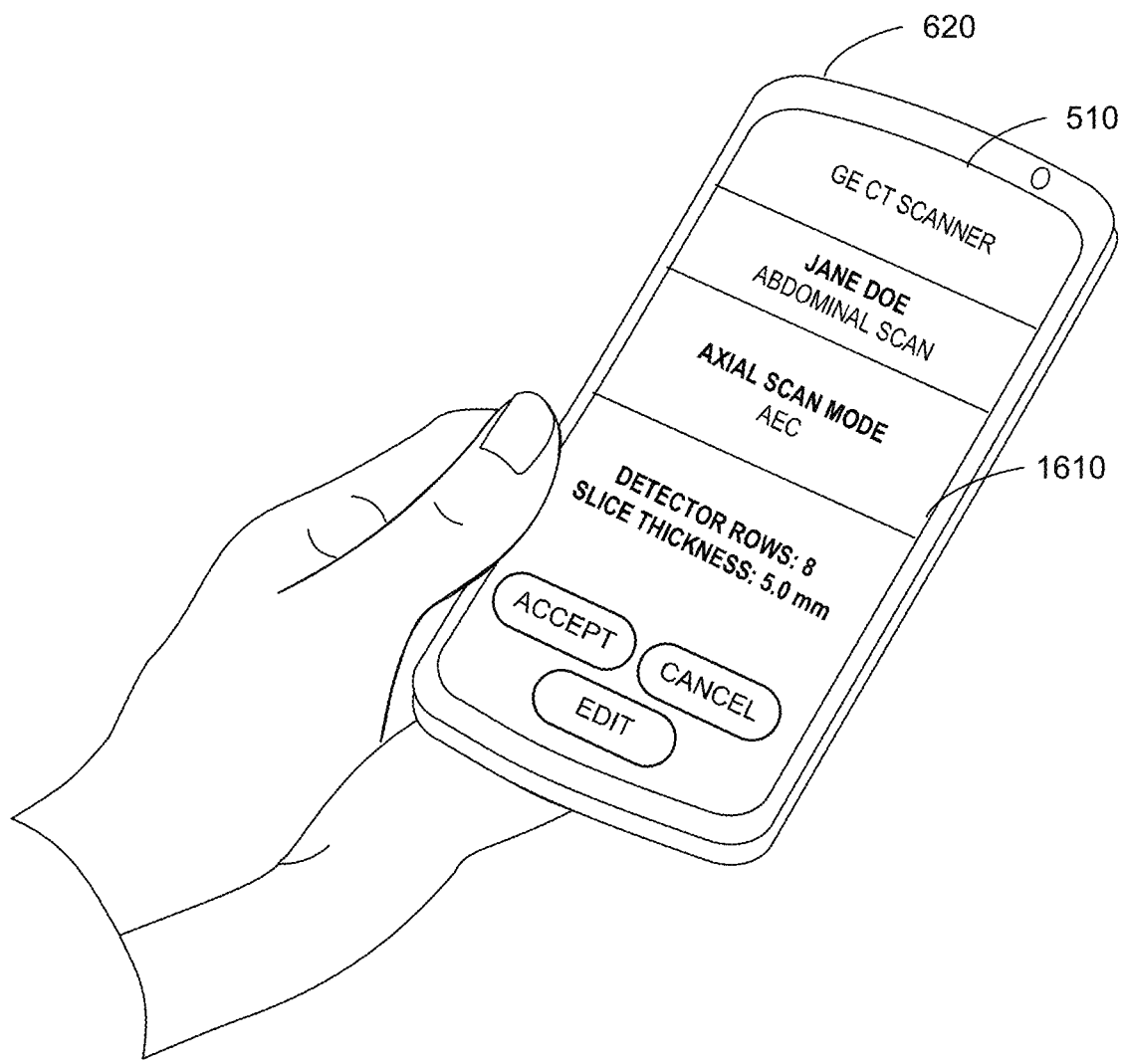
FIGS. 16-17 show example user devices with interfaces facilitating interaction with the digital assistant of FIGS. 1-7.

Output can be provided via the example user interface 510 to display information to a user (e.g., settings/configuration information, program options, skills, etc.), facilitate feedback and/or other interaction for digital twin 230 model development, medical equipment 120 configuration/operation, etc. FIG. 16 depicts an example implementation of the user device 620 as a smartphone with the graphical user interface 510. As shown in the example of FIG. 16, the example interface 510 provides an imaging system configuration 1610 that can be accepted, canceled, and/or edited by a user via the interface 510.

Figure 17:
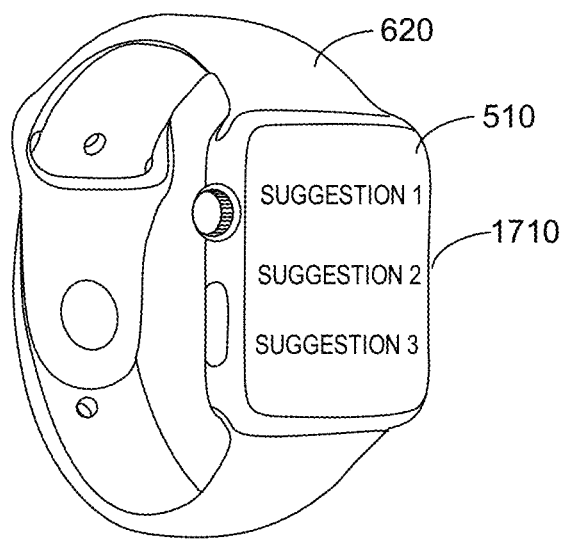

FIG. 17 shows another example implementation of the user device 620 as a smart watch with the graphical user interface 510. A user can select a suggestion 1710 to trigger a corresponding skill of the digital assistant 110 via the smart watch.

Thus, certain examples provide a digital assistant enabled with skills, macros, and models to drive user workflows, medical equipment configuration and operation, exam documentation, etc. For example, skills can include hemodynamic configuration and monitoring, diagnostic catheterization, coronary procedure, peripheral procedure, electrophysiology procedure, pre- and post-procedure documentation, etc. An example skill can combine multiple procedural steps in sequential order, for example. Several skills can be linked together, for example.

For example, a skill related to hemodynamic and electrophysiology recording can provide pre-case setup starting before the patient is positioned with respect to a table for the procedure. The example skill can automatically configure who is working on the case, what type of case, begin capture of patient vitals, capture an ECG baseline, etc. Example post-case actions can include capture of results and formatting of data for the patient's medical record, documentation of supplies used, staff involved, medications, etc. An example diagnostic catheterization skill can include automatic configuration of pressure labels (e.g. set Pressure 1 to left ventricle for a left heart catheterization of the left ventricle, etc.), set scales, perform measurements, etc. An example interventional catheterization skill can include automated documentation, guide catheter insertion, interventional guidewire insertion, measure aorta (AO), coronary artery visualization, guide stent catheter insertion, open coronary interventional window, open graft interventional window, remove stent deployment system, etc.

While example implementations are disclosed and described herein, processes and/or devices disclosed and described herein can be combined, divided, re-arranged, omitted, eliminated and/or implemented in any other way. Further, components disclosed and described herein can be implemented by hardware, machine readable instructions, software, firmware and/or any combination of hardware, machine readable instructions, software and/or firmware. Thus, for example, components disclosed and described herein can be implemented by analog and/or digital circuit(s), logic circuit(s), programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the components is/are hereby expressly defined to include a tangible computer readable storage device or storage disk such as a memory, a digital versatile disk (DVD), a compact disk (CD), a Blu-ray disk, etc. storing the software and/or firmware.

Flowcharts representative of example machine readable instructions for implementing components are disclosed and described herein. In the examples, the machine readable instructions include a program for execution by a processor. The program may be embodied in machine readable instructions stored on a tangible computer readable storage medium such as a CD-ROM, a floppy disk, a hard drive, a digital versatile disk (DVD), a Blu-ray disk, or a memory associated with the processor, but the entire program and/or parts thereof could alternatively be executed by a device other than the processor and/or embodied in firmware or dedicated hardware. Further, although the example program is described with reference to flowchart(s), many other methods of implementing the components disclosed and described herein may alternatively be used. For example, the order of execution of the blocks may be changed, and/or some of the blocks described may be changed, eliminated, or combined. Although the flowchart(s) depict example operations in an illustrated order, these operations are not exhaustive and are not limited to the illustrated order. In addition, various changes and modifications may be made by one skilled in the art within the spirit and scope of the disclosure. For example, blocks illustrated in the flowchart may be performed in an alternative order or may be performed in parallel.

As mentioned above, the example process(es) can be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example process(es) can be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended. In addition, the term "including" is open-ended in the same manner as the term "comprising" is open-ended.

Figure 18:
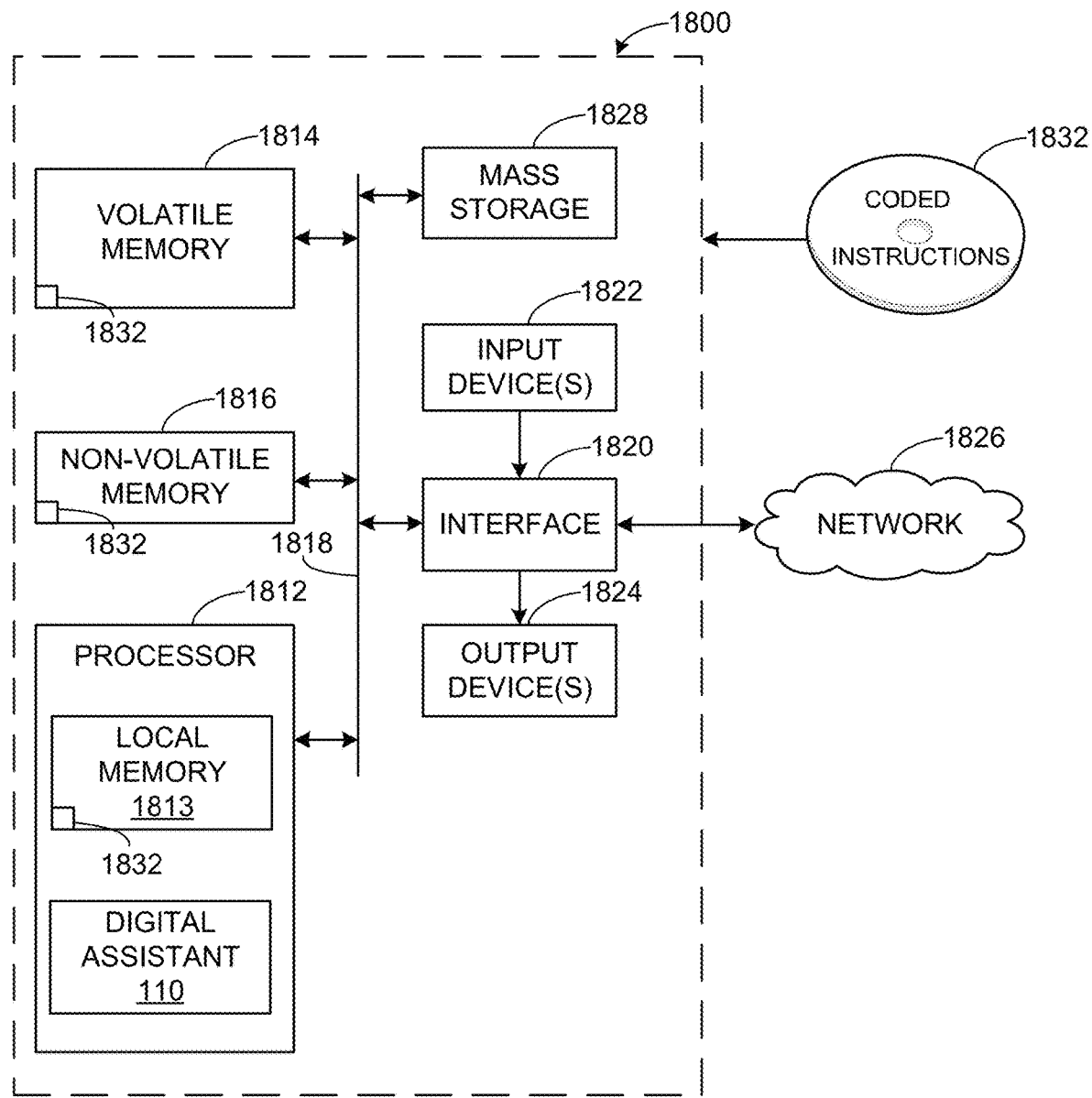
FIG. 18 is a block diagram of an example processor platform capable of executing instructions to implement the example systems and methods disclosed and described herein.

FIG. 18 is a block diagram of an example processor platform 1800 structured to execute the instructions of FIGS. 8-15 to implement, for example the example digital assistant 110 and other systems, apparatus, etc., of FIGS. 1-7. The processor platform 1800 can be, for example, a server, a personal computer, a workstation, a self-learning machine (e.g., a neural network), a mobile device (e.g., a cell phone, a smart phone, a tablet such as an iPad'), a personal digital assistant (PDA), an Internet appliance, a gaming console, a personal video recorder, a set top box, a headset or other wearable device, or any other type of computing device.

The processor platform 1800 of the illustrated example includes a processor 1812. The processor 1812 of the illustrated example is hardware. For example, the processor 1812 can be implemented by one or more integrated circuits, logic circuits, microprocessors, GPUs, DSPs, or controllers from any desired family or manufacturer. The hardware processor may be a semiconductor based (e.g., silicon based) device. In this example, the processor 1812 implements the example digital assistant 110 but can also be used to implement other systems and/or subsystems (e.g., the medical equipment 120, part of the digital assistant 110, etc.) disclosed herein.

The processor 1812 of the illustrated example includes a local memory 1813 (e.g., a cache). The processor 1812 of the illustrated example is in communication with a main memory including a volatile memory 1814 and a non-volatile memory 1816 via a bus 1818. The volatile memory 1814 may be implemented by SDRAM, DRAM, RDRAM®, and/or any other type of random access memory device. The non-volatile memory 1816 may be implemented by flash memory and/or any other desired type of memory device. Access to the main memory 1814, 1816 is controlled by a memory controller.

The processor platform 1800 of the illustrated example also includes an interface circuit 1820. The interface circuit 1820 may be implemented by any type of interface standard, such as an Ethernet interface, a USB, a Bluetooth® interface, an NFC interface, and/or a PCI express interface.

In the illustrated example, one or more input devices 1822 are connected to the interface circuit 1820. The input device(s) 1822 permit(s) a user to enter data and/or commands into the processor 1812. The input device(s) can be implemented by, for example, an audio sensor, a microphone, a camera (still or video), a keyboard, a button, a mouse, a touchscreen, a track-pad, a trackball, isopoint, and/or a voice recognition system.

One or more output devices 1824 are also connected to the interface circuit 1820 of the illustrated example. The output devices 1824 can be implemented, for example, by display devices (e.g., an LED, an OLED, an LCD, a CRT display, an IPS display, a touchscreen, etc.), a tactile output device, a printer, and/or speaker. The interface circuit 1820 of the illustrated example, thus, typically includes a graphics driver card, a graphics driver chip, and/or a graphics driver processor.

The interface circuit 1820 of the illustrated example also includes a communication device such as a transmitter, a receiver, a transceiver, a modem, a residential gateway, a wireless access point, and/or a network interface to facilitate exchange of data with external machines (e.g., computing devices of any kind) via a network 1826. The communication can be via, for example, an Ethernet connection, a DSL connection, a telephone line connection, a coaxial cable system, a satellite system, a line-of-site wireless system, a cellular telephone system, etc.

The processor platform 1800 of the illustrated example also includes one or more mass storage devices 1828 for storing software and/or data. Examples of such mass storage devices 1828 include floppy disk drives, hard drive disks, compact disk drives, Blu-ray disk drives, RAID systems, and DVD drives.

The machine executable instructions 1832 of FIGS. 8-15 can be stored in the mass storage device 1828, in the volatile memory 1814, in the non-volatile memory 1816, and/or on a removable non-transitory computer readable storage medium such as a CD or DVD.

From the foregoing, it will be appreciated that example methods, apparatus and articles of manufacture have been disclosed that generate and drive medical equipment configuration and interaction using with new, technologically improved interfaces and digital twin/AI models. As such, certain examples improve the capabilities, efficiency, and effectiveness of processor system, memory, and other associated circuitry by leveraging artificial intelligence models, transformations and expansions of equipment configurations, healthcare protocols, comparative analysis of best practices/preferences, etc. The disclosed methods, apparatus and articles of manufacture are accordingly directed to one or more improvement(s) in the functioning of a computer and/or other processor and its associated interface. The apparatus, methods, systems, instructions, and media disclosed herein are not implementable in a human mind and are not able to be manually implemented by a human user.

As disclosed above, certain examples provide a portable digital assistant that can be implemented on one or more platforms such as a smartphone, smart watch, tablet, laptop, portable storage (e.g., flash drive, thumb drive, etc.), etc. In certain examples, the digital assistant leverages a cloud infrastructure and can be mobilized through a smart phone, smart watch, portable storage drive that can be carried and inserted in a local laptop/desktop/tablet, etc. The digital assistant can then dynamically react to its location and/or context to provide relevant configuration and/or instructions to a user, medical equipment, etc. The digital assistant can provide a calculation engine and/or semantic engine built on analytics to process stored and incoming information, compare the information to prior data in the same or similar task/event, and drive dynamically interactive medical equipment configuration and associated workflow execution.

Certain examples provide a configuration hierarchy for medical equipment via the digital assistant. For example, a generic plugin can be provided including a generic model of skills/settings/functions for a type of medical equipment. Additional specific plugins for that type of medical equipment can include location-specific variants, application-specific variants, user-specific variants, other context-specific variants, such that the digital assistant can dynamically configure the medical equipment for the user more precisely for a particular location, particular protocol/workflow, particular user preference, etc.

As such, a framework of problem domain-specific skills (e.g., ablation, x-ray imaging, waveform analysis, study configuration, etc.) are tied to interact with the digital assistant to make the skills interactive and suited for a flexible purpose. The digital assistant and its models/skills are portable and equipment agnostic but user-specific. Thus, the digital assistant serves as a personal assistant to configure for a particular user but with respect to a flexible variety of equipment, protocols, plans, environments, etc.

Certain examples process schedule information to determine configuration/settings for equipment involved in events in the schedule. The digital assistant identifies resources and tasks involved and leverages models and/or other stored data store information to determine configuration, sequence, etc. One or more prior configurations can be leveraged but can be adapted for equipment type/version, location, purpose, user, etc.

Certain examples provide an adaptive, learning digital assistant that captures settings and learns from actions, results, feedback, etc., to build and interpret patterns to form models and/or other constructs representative of configurations/settings, sequences/workflows, etc. As such, the digital assistant provides a dynamic framework to drive medical equipment configuration and associated workflows. Skills, macros, models, etc., form a blueprint to configure equipment, execute a case/protocol/workflow, etc., and are selected and leveraged by the digital assistant based on context such as user, location, patient, equipment, reason for exam/treatment, etc. The digital assistant can select/activate skills individually and/or in combination.

For example, a machine learning and algorithmic combination can be used by the digital assistant to configure a computer to form a waveform analysis server that receives and processes data such as electrocardiograms (ECGs). The digital assistant triggers analysis of waveform data (e.g., ECG data, etc.) and perform a comparison based on a combination of a waveform analysis skill and a waveform comparison skill, for example.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

What is claimed is:

1. A digital assistant apparatus comprising:
   memory including instructions; and
   at least one processor to execute the instructions to at least:
   form a model of at least one aspect of a medical equipment;
   transform the model into a configuration for the medical equipment to perform a task;
   process input to adjust the configuration;
   provide the configuration to the medical equipment;
   monitor execution of the task by the medical equipment; and
   adjust the configuration of the medical equipment based on the monitored execution;
   wherein the model is included in a digital twin of the medical equipment and
   wherein the digital twin represents a digital model of the medical equipment,
   wherein the medical equipment comprises a plurality of medical equipment types;
   wherein the input includes at least one of location, user, or version of the medical equipment.

2. The apparatus of claim 1, wherein the model is provided as a plugin to the digital twin.

3. The apparatus of claim 1, wherein the input includes at least one of input from the medical equipment and input from a user device.

4. The apparatus of claim 1, wherein the model is a first model, the configuration is a first configuration, and the medical equipment is a first medical equipment, and wherein the instructions, when executed, cause the at least one processor to generate a second model from a second configuration captured from a second medical equipment.

5. The apparatus of claim 1, wherein the model is an artificial intelligence model.

6. The apparatus of claim 1, wherein the instructions, when executed, cause the at least one processor to adjust the model based on at least one of feedback, location, or version.

7. The apparatus of claim 1, wherein the instructions, when executed, cause the at least one processor to provide the configuration for interactive display and approval via a graphical user interface.

8. The apparatus of claim 7, wherein feedback via the graphical user interface is to form the input to adjust the configuration.

9. The apparatus of claim 1, wherein the location comprises a location of a physician that interacts with the medical equipment.

10. At least one tangible computer-readable storage medium comprising instructions that, when executed, cause at least one processor to at least:
    form a model of at least one aspect of a medical equipment;
    transform the model into a configuration for the medical equipment to perform a task;
    process input to adjust the configuration;
    provide the configuration to the medical equipment;
    monitor execution of the task by the medical equipment; and
    adjust the configuration of the medical equipment based on the monitored execution,
    wherein the model is included in a digital twin of the medical equipment and wherein the digital twin represents a digital model of the medical equipment, wherein the medical equipment comprises a plurality of medical equipment types, wherein the input includes at least one of location, user, or version of the medical equipment.

11. The at least one computer-readable storage medium of claim 10, wherein the model is provided as a plugin to the digital twin.

12. The at least one computer-readable storage medium of claim 10, wherein the input includes at least one of input from the medical equipment and input from a user device.

13. The at least one computer-readable storage medium of claim 10, wherein the model is a first model, the configuration is a first configuration, and the medical equipment is a first medical equipment, and wherein the instructions, when executed, cause the at least one processor to generate a second model from a second configuration captured from a second medical equipment.

14. The at least one computer-readable storage medium of claim 10, wherein the model is an artificial intelligence model.

15. The at least one computer-readable storage medium of claim 10, wherein the instructions, when executed, cause the at least one processor to adjust the model based on at least one of feedback, location, or version.

16. The at least one computer-readable storage medium of claim 10, wherein the instructions, when executed, cause the at least one processor to provide the configuration for interactive display and approval via a graphical user interface.

17. The at least one computer-readable storage medium of claim 10, wherein the plurality of medical equipment types comprises a combination medical equipment types.

18. A computer-implemented method to configure medical equipment using a digital assistant, the method comprising:
    forming a model of at least one aspect of a medical equipment types;
    transforming the model into a configuration for the medical equipment to perform a task;
    processing input to adjust the configuration;
    providing the configuration to the medical equipment;
    monitoring execution of the task by the medical equipment; and
    adjusting the configuration of the medical equipment based on the monitored execution;
    wherein the model is included in a digital twin of the medical equipment and wherein the digital twin represents a digital model of the medical equipment, wherein the medical equipment comprises a plurality of medical equipment types, wherein the input includes at least one of location, user, or version of the medical equipment.

19. The apparatus of claim 18, wherein the plurality of medical equipment types comprises, catheterization lab equipment, medical imaging devices, medical tools, medical information systems, a picture archiving and communication system (PACS), a radiology information system (RIS), an electronic medical record (EMR) system, a health information system (HIS), a laboratory information system (LIS), a cardiovascular information system (CVIS), and ablation devices.

\* \* \* \* \*